(12) United States Patent
Saito

(10) Patent No.: US 9,295,437 B2
(45) Date of Patent: Mar. 29, 2016

(54) X-RAY IMAGING APPARATUS, WEDGE FILTER APPARATUS, AND METHOD OF CONTROLLING WEDGE FILTER

(71) Applicants: Kabushiki Kaisha Toshiba, Minato-ku (JP); Toshiba Medical Systems Corporation, Otawara-shi (JP)

(72) Inventor: Yasuo Saito, Nasushiobara (JP)

(73) Assignees: KABUSHIKI KAISHA TOSHIBA, Minato-ku (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/282,725

(22) Filed: May 20, 2014

(65) Prior Publication Data
US 2014/0254747 A1    Sep. 11, 2014

Related U.S. Application Data

(63) Continuation of application No. PCT/JP2013/076883, filed on Oct. 2, 2013.

(30) Foreign Application Priority Data

Oct. 2, 2012   (JP) .................................. 2012-220220

(51) Int. Cl.
*A61B 6/00*   (2006.01)
*G21K 1/04*   (2006.01)
(Continued)

(52) U.S. Cl.
CPC ............... *A61B 6/4035* (2013.01); *A61B 6/032* (2013.01); *A61B 6/035* (2013.01); *A61B 6/4241* (2013.01); *A61B 6/482* (2013.01); *A61B 6/542* (2013.01); *G21K 1/046* (2013.01); *G21K 1/10* (2013.01); *A61B 6/4233* (2013.01); *A61B 6/488* (2013.01); *A61B 6/582* (2013.01)

(58) Field of Classification Search
CPC ....................................................... A61B 6/4241
See application file for complete search history.

(56) References Cited

U.S. PATENT DOCUMENTS

| | | |
|---|---|---|
| 7,403,589 B1 | 7/2008 | Short et al. |
| 8,660,235 B2 | 2/2014 | Koehler |

(Continued)

FOREIGN PATENT DOCUMENTS

| | | |
|---|---|---|
| CN | 101273898 A | 10/2008 |
| CN | 102596040 A | 7/2012 |

(Continued)

OTHER PUBLICATIONS

International Search Report mailed Oct. 29, 2013 for PCT/JP2013/076883 filed Oct. 2, 2013 with English Translation.

(Continued)

*Primary Examiner* — Hoon Song
(74) *Attorney, Agent, or Firm* — Oblon, McClelland, Maier & Neustadt, L.L.P.

(57) ABSTRACT

According to one embodiment, a flexible wedge filter is arranged between an X-ray tube and an examinee to attenuate a dose according to an X-ray from the X-ray tube. The flexible wedge filter has a plurality of filter modules 39 having a configuration capable of individually changing an X-ray transmission path length in an X-ray shielding material. The PCCT gantry controller individually operates the plurality of filter modules such that a dose according to an X-ray incident to an X-ray detector from the X-ray tube via the examinee is distributed substantially uniformly in spatial.

12 Claims, 18 Drawing Sheets

(51) Int. Cl.
*G21K 1/10* (2006.01)
*A61B 6/03* (2006.01)

(56) References Cited

U.S. PATENT DOCUMENTS

2010/0282972 A1* 11/2010 Carmi et al. .................. 250/362
2011/0206259 A1* 8/2011 Mistretta et al. ............. 382/131

FOREIGN PATENT DOCUMENTS

JP 2008-246206 A 10/2008
WO WO 2011/055267 A1 5/2011

OTHER PUBLICATIONS

International Written Opinion mailed Oct. 29, 2013 for PCT/JP2013/076883 filed Oct. 2, 2013.
English translation of International Preliminary Report on Patentability and Written Opinion issued Apr. 16, 2015 in PCT/JP2013/076883 (original language Written Opinion previously filed May 20, 2014).
Combined Office Action and Search Report issued on Jul. 1, 2015 in Chinese Patent Application No. 201380002137.4 with English translation of category of cited documents.

* cited by examiner

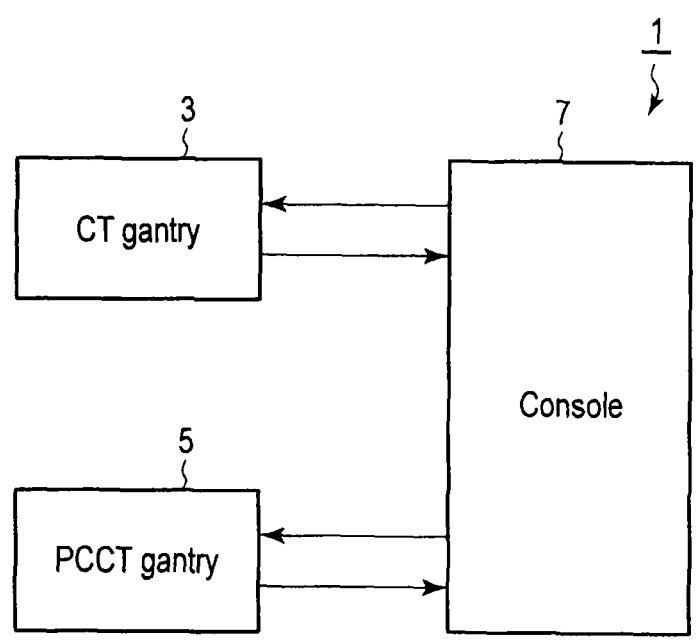
F I G. 1

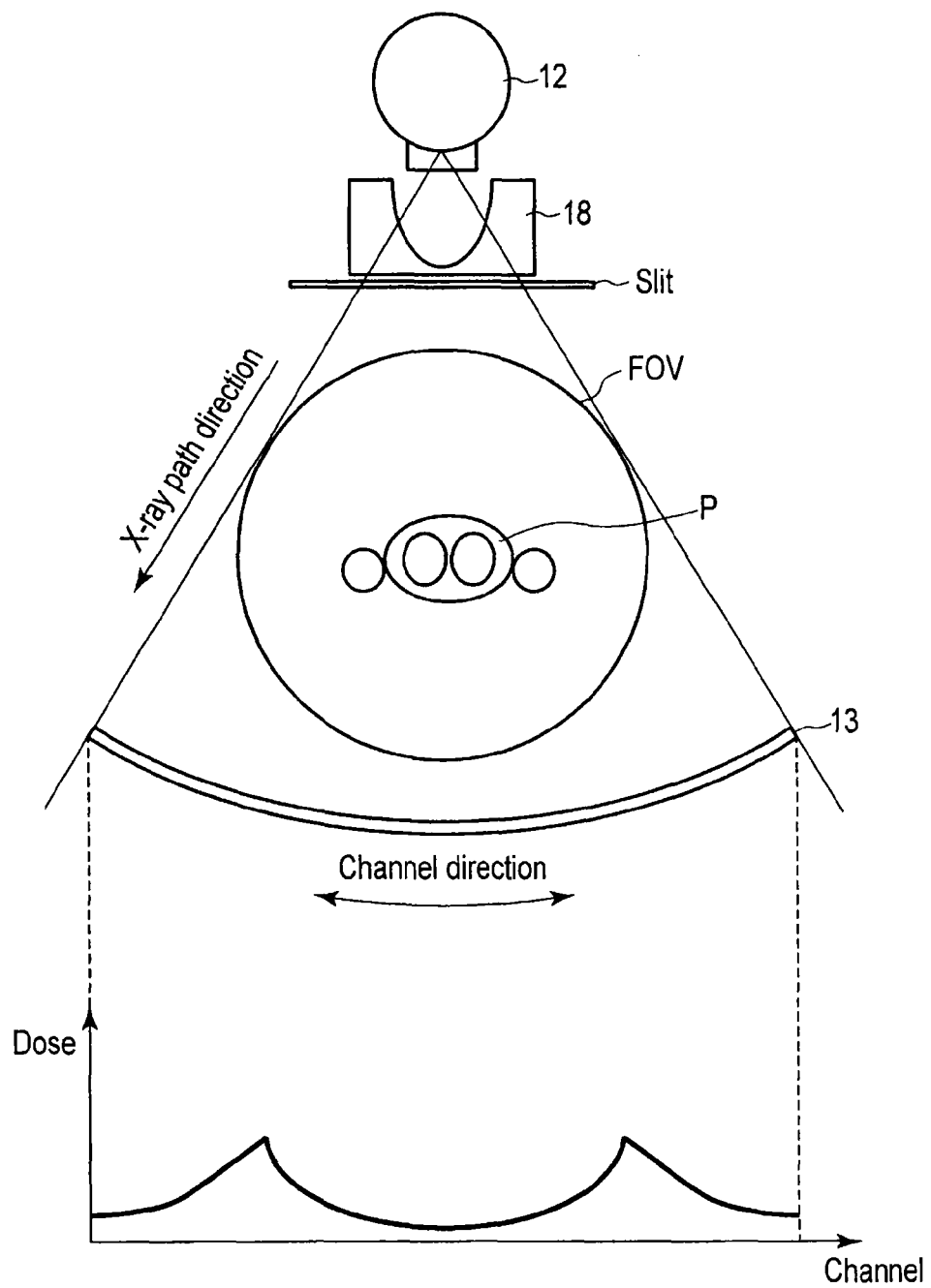
F I G. 6

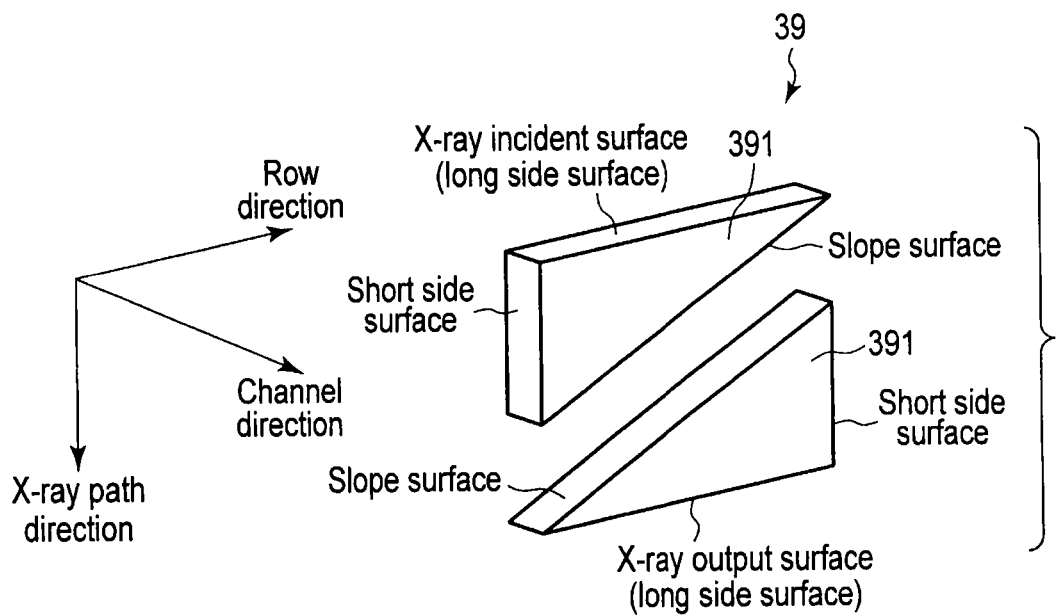
F I G. 10

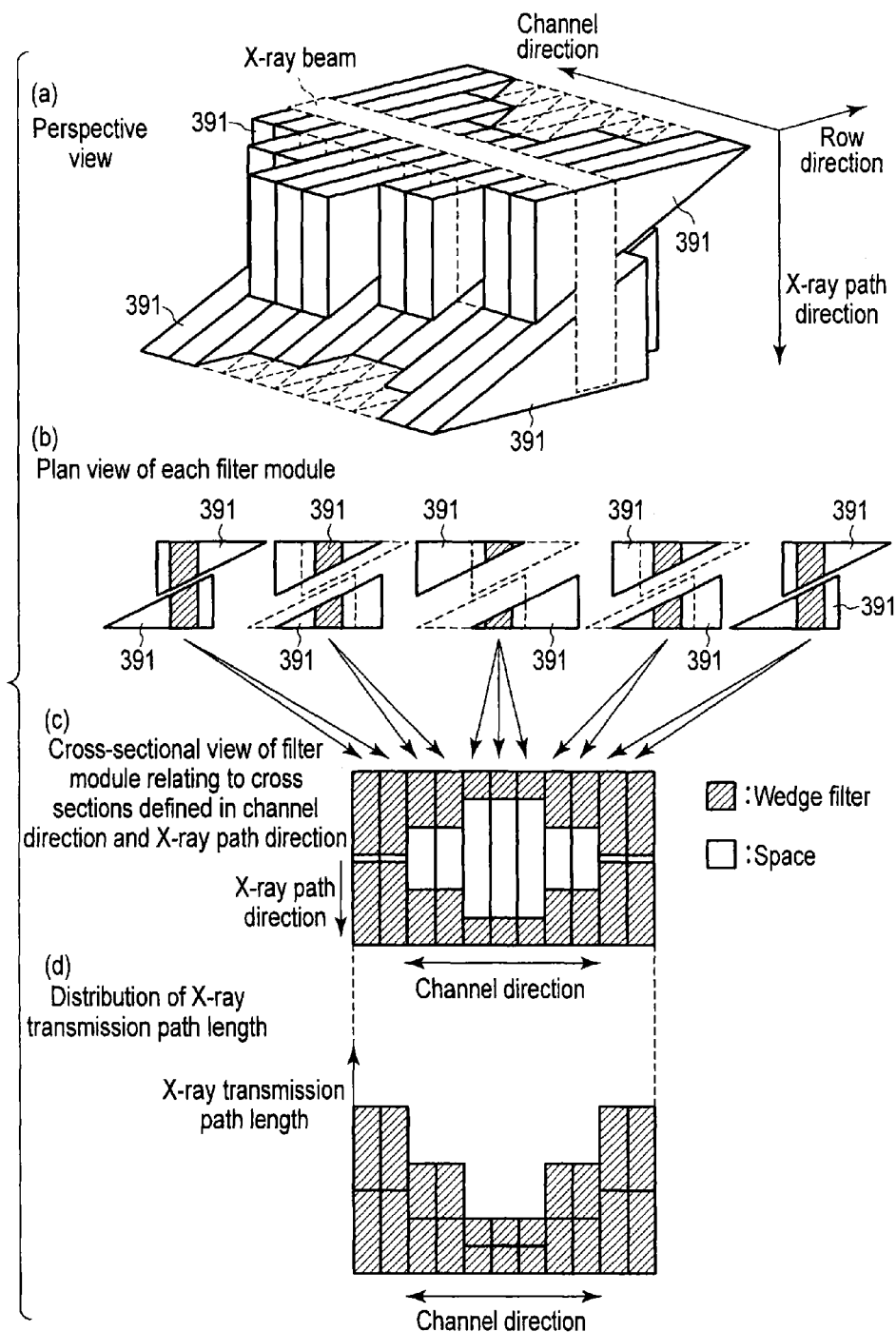
F I G. 14

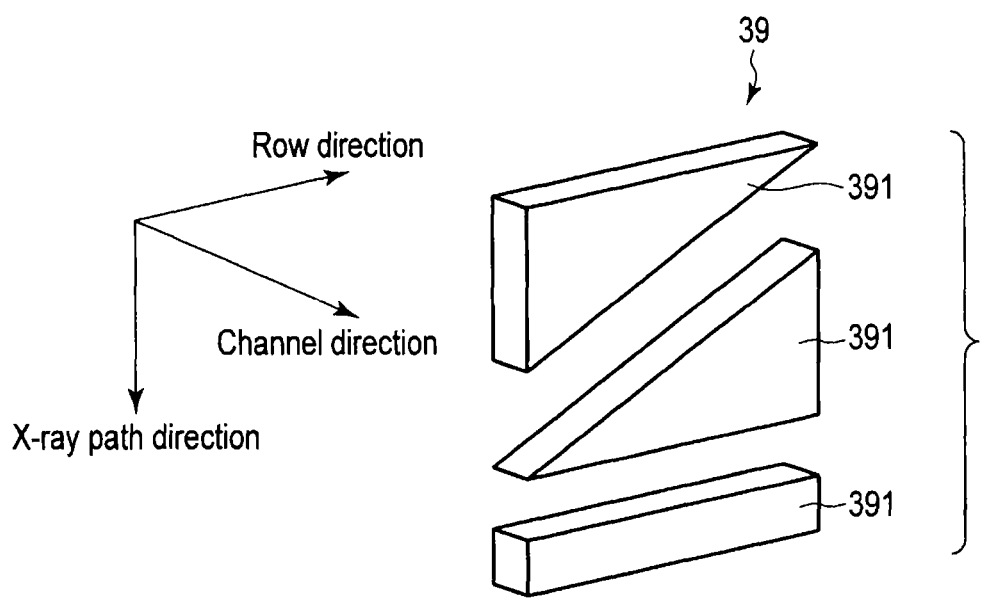
F I G. 16

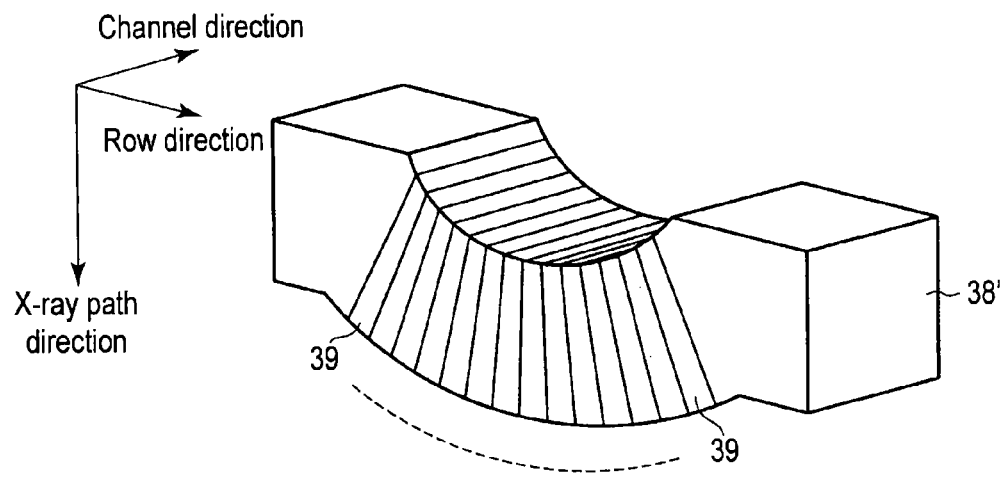
F I G. 19
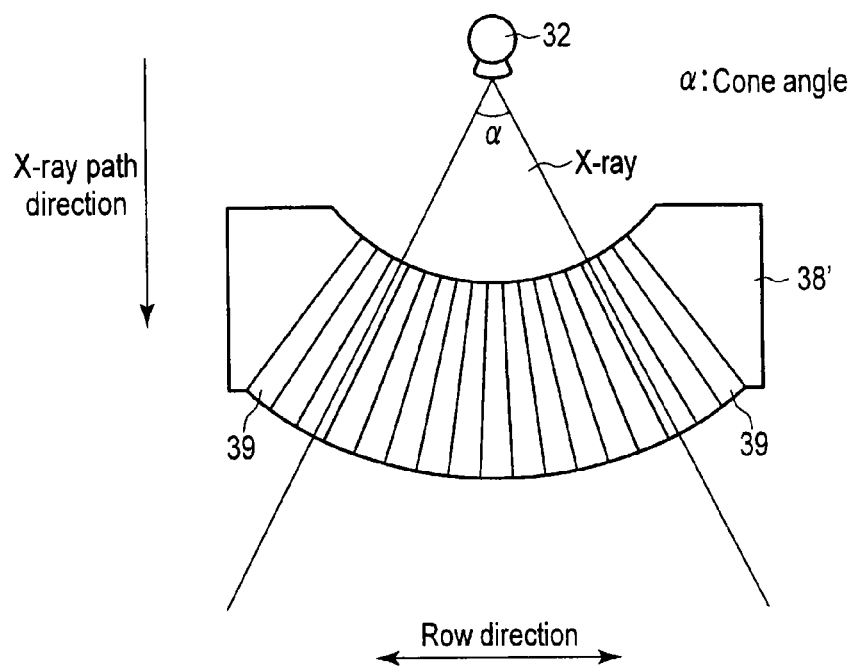
F I G. 20

X-RAY IMAGING APPARATUS, WEDGE FILTER APPARATUS, AND METHOD OF CONTROLLING WEDGE FILTER

CROSS-REFERENCE TO RELATED APPLICATIONS

This application is a Continuation application of PCT Application No. PCT/JP2013/076883, filed Oct. 2, 2013 and based upon and claims the benefit of priority from the Japanese Patent Application No. 2012-220220, filed Oct. 2, 2012, the entire contents of all of which are incorporated herein by reference.

FIELD

Embodiments described herein relate generally to an X-ray imaging apparatus, a wedge filter apparatus, and a method of controlling a wedge filter.

BACKGROUND

In an X-ray computed tomography (CT), it is demanded to improve quantitativity of a CT value. As an imaging method for improving quantitativity of the CT value, for example, there have been proposed a dual energy CT (DECT) and a photon counting CT (PCCT). The DECT is for simply discriminating a material using projection data of two types of X-ray energy. The PCCT is an improved imaging method having higher quantitativity compared to the DECT. As well known in the art, in the PCCT, it is necessary to count X-ray photons one by one. In order to prevent an overflow in the X-ray photon measurement (count loss or pile-up of X-ray photons), an upper limit of a dose rate (dose on unit area per unit time) is inevitably set to be low. Meanwhile, the dose according to the X-ray transmitting through an examinee and arriving at an X-ray detector has a dynamic range of 16 bits or wider. For this reason, data of a high dose with a high overflow risk and data of a significantly low dose with a lot of noises are mixed in data used in an image reconstruction of the PCCT. When the PCCT data acquisition is executed under a condition for avoiding an overflow, data of the significantly low dose becomes dominant, and a noise caused by a measurement error increases.

It is an object of embodiments to provide an X-ray imaging apparatus, a wedge filter apparatus, and a method of controlling a wedge filter capable of reducing an overflow risk and a dynamic range.

BRIEF DESCRIPTION OF THE DRAWINGS

FIG. 1 is a diagram illustrating a configuration of an X-ray computed tomography apparatus according to the present embodiment.

FIG. 6 is a diagram illustrating a simplified configuration of the CT gantry having the fixed wedge filter of FIG. 2 and an incident dose distribution.

FIG. 10 is a schematic perspective view illustrating the filter module of FIGS. 8 and 9.

FIG. 14 is a diagram for describing control of an X-ray transmission path length distribution in a channel direction using the flexible wedge filter performed in step SA6 of FIG. 12.

FIG. 16 is a perspective view illustrating another filter module according to Modification 1.

FIG. 19 is a schematic perspective view illustrating a flexible wedge filter according to Modification 3.

FIG. 20 is a plan view illustrating the flexible wedge filter according to Modification 3 as seen in a row direction.

DETAILED DESCRIPTION

Figure 2:
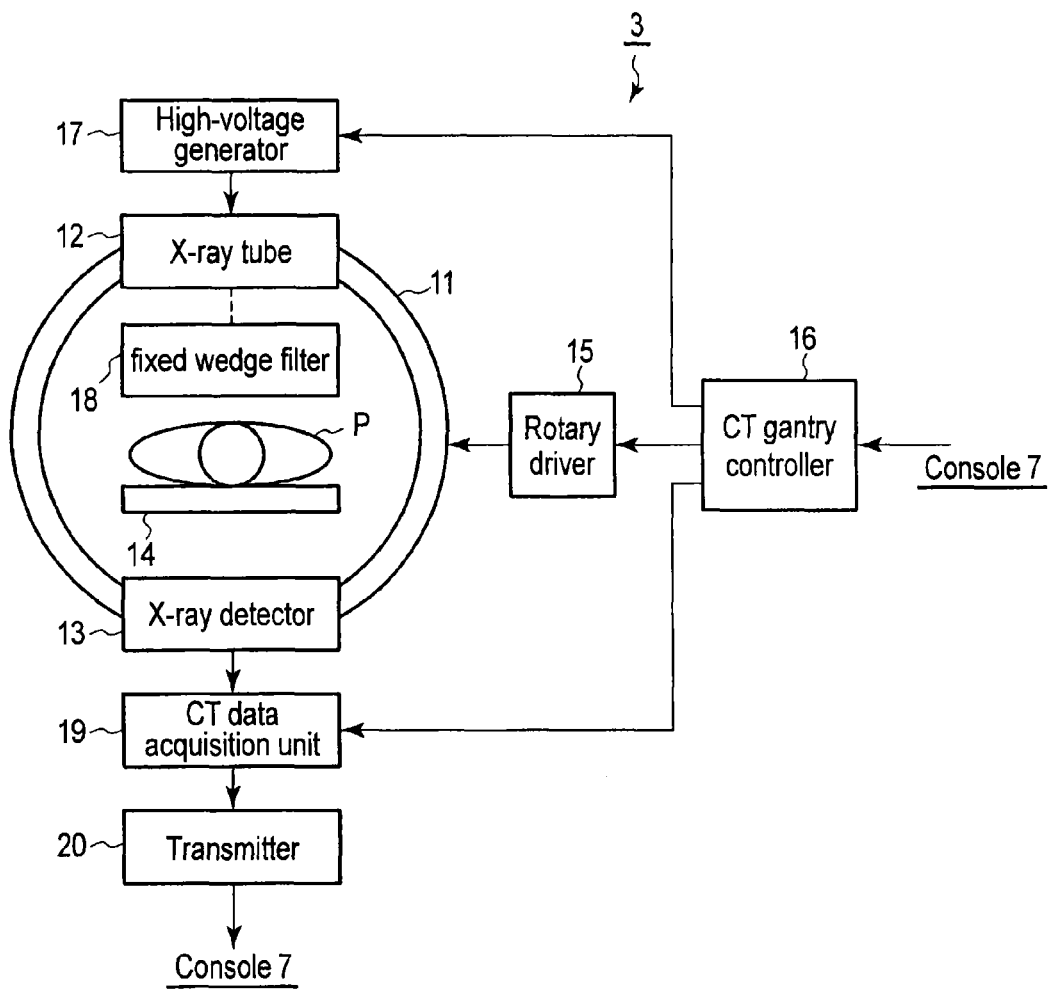
FIG. 2 is a diagram illustrating a configuration of a CT gantry of FIG. 1.

In general, according to one embodiment, an X-ray imaging apparatus includes an X-ray tube, an X-ray detector, a support mechanism, a data acquisition unit, a wedge filter unit, and a controller. The X-ray tube is configured to generate an X-ray. The X-ray detector is configured to detect the X-ray which is generated from the X-ray tube and transmits through an examinee. The support mechanism is configured to support the X-ray tube and the X-ray detector. The data acquisition unit is configured to acquire a dataset relating to a count of an X-ray photon for each of a plurality of energy bands included in an energy spectrum of the X-ray generated from the X-ray tube. The wedge filter unit is configured to be arranged between the X-ray tube and the examinee to attenuate a dose according to an X-ray from the X-ray tube and include a plurality of filter modules having a configuration capable of individually changing an X-ray transmission path length in an X-ray shielding material. The controller is configured to individually operate the plurality of filter modules such that a dose according to an X-ray incident to the X-ray detector from the X-ray tube via the examinee is distributed substantially uniformly in spatial.

Hereinafter, an X-ray imaging apparatus, a wedge filter apparatus, and a method of controlling a wedge filter according to the present embodiment will be described with reference to the accompanying drawings.

As an X-ray imaging apparatus according to the present embodiment, a medical image diagnosis apparatus using an X-ray, that is, an X-ray computed tomography (CT) apparatus and an X-ray diagnosis apparatus may be employed. In order to describe embodiments in detail below, an X-ray computed tomography apparatus will be described by way of example as the X-ray imaging apparatus according to the present embodiment.

FIG. 1 is a diagram illustrating a configuration of the X-ray computed tomography apparatus 1 according to the present embodiment. As illustrated in FIG. 1, the X-ray computed tomography apparatus 1 according to the present embodiment includes a CT gantry 3, a PCCT gantry 5, and a console 7. The CT gantry 3 and the PCCT gantry 5 are connected to the console 7 via a network. The CT gantry 3 and the PCCT gantry 5 are installed in the same or different examination rooms. The console 7 is installed, for example, in a control room neighboring to the examination room. The CT gantry 3 has an imaging mechanism for performing typical CT data acquisition, that is, integration type data acquisition (electric current type data acquisition). The PCCT gantry 5 has an imaging mechanism for performing photon-counting computed tomography (hereinafter, referred to as "PCCT"). The console 7 is a computer device that individually controls the CT gantry 3 and the PCCT gantry 5. In this manner, the X-ray computed tomography apparatus 1 is a complex system capable of executing both the typical CT imaging using the CT gantry 3 and the PCCT imaging using the PCCT gantry 5.

FIG. 2 is a diagram illustrating a configuration of the CT gantry 3 according to the present embodiment. As illustrated in FIG. 2, the CT gantry 3 has a configuration similar to that of a typical integration type CT gantry. That is, the CT gantry 3 is provided with a rotary frame 11 having a substantially cylindrical shape. In the rotary frame 11, an X-ray tube 12 and an X-ray detector 13 are installed to face each other by interposing a rotation axis Z1. A part of a space area in the inner circumference of the rotary frame 11 is set to a field of view (FOV). A top plate 14 is positioned inside the bore of the rotary frame 11. An examinee P is laid on the top plate 14. The top plate 14 moves such that an imaging region of the examinee P laid on the top plate 14 is included in the FOV. The rotary frame 11 is supplied with a driving signal from the rotary driver 15 and is rotated at a constant angular velocity with respect to the rotation axis Z1. The rotary driver 15 rotates the rotary frame 11 at a constant angular velocity with respect to the rotation axis Z1 in response to control of the CT gantry controller 16.

The X-ray tube 12 receives a high voltage applied from the high-voltage generator 17 and is supplied with a filament electric current to generate an X-ray. The high-voltage generator 17 applies a high voltage to the X-ray tube 12 in response to control of the CT gantry controller 16 and supplies the filament electric current to the X-ray tube 12 in response to control of the CT gantry controller 16.

A fixed wedge filter 18 is provided between the X-ray tube 12 and the examinee P. The fixed wedge filter 18 is a wedge filter having a fixed shape. It should be noted that another filter such as a slit may be provided between the fixed wedge filter 18 and the examinee P.

The X-ray detector 13 detects an X-ray generated from the X-ray tube 12. A plurality of detection elements arranged two-dimensionally are mounted on the X-ray detector 13. Each detection element detects an X-ray from the X-ray tube 12 and generates an electric signal depending on the energy of the detected X-ray. The generated electric signal is supplied to a CT data acquisition unit (DAS: data acquisition system) 19. The CT data acquisition unit 19 reads the electric signal using the X-ray detector 13 in response to control of the CT gantry controller 16 and acquires the read electric signal for each view in an integral mode. More specifically, in the integral mode, the CT data acquisition unit 19 integrates the electric signal of each detection element for each of a plurality of views to generate an integral signal. The CT data acquisition unit 19 converts the acquired analog electric signal (integral signal) into digital data. The digital data is called CT raw data. The CT raw data is supplied to the console 7 via a contactless type transmitter 20.

Figure 3:
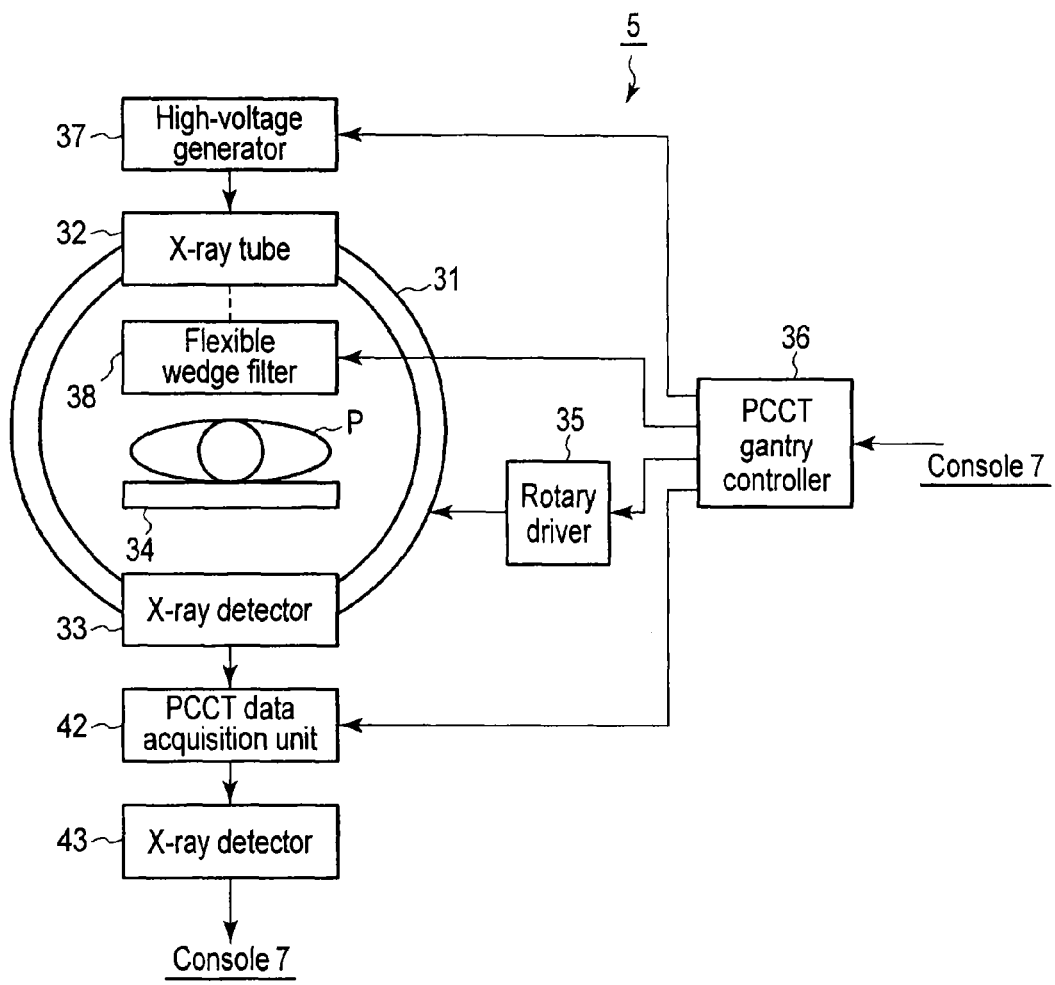
FIG. 3 is a diagram illustrating a configuration of a PCCT gantry of FIG. 1.

FIG. 3 is a diagram illustrating a configuration of the PCCT gantry 5 according to the present embodiment. As illustrated in FIG. 3, the PCCT gantry 5 is provided with a rotary frame 31 having a substantially cylindrical shape. In the rotary frame 31, an X-ray tube 32 and an X-ray detector 33 are installed to face each other by interposing a rotation axis Z2. A part of a space area in the inner circumference of the rotary frame 31 is set as a field of view (FOV). A top plate 34 is positioned inside the opening of the rotary frame 31. An examinee P is laid on the top plate 34. The top plate 34 moves such that an imaging region of the examinee P laid on the top plate 34 is included in the FOV. The rotary frame 31 is supplied with a driving signal from the rotary driver 35 and is rotated at a constant angular velocity with respect to the rotation axis Z2. The rotary driver 35 rotates the rotary frame 31 at a constant angular velocity with respect to the rotation axis Z2 in response to control of the PCCT gantry controller 36.

The X-ray tube 32 receives a high voltage applied from the high-voltage generator 37 and is supplied with a filament electric current to generate an X-ray. The high-voltage generator 37 applies a high voltage to the X-ray tube 32 in response to control of the PCCT gantry controller 36 and supplies the filament electric current to the X-ray tube 32 in response to control of the PCCT gantry controller 36.

A flexible wedge filter 38 is provided between the X-ray tube 32 and the examinee P in order to attenuate a dose according to the X-ray from the X-ray tube 32. The flexible wedge filter 38 is a wedge filter capable of changing a shape. It should be noted that another filter such as a slit may also be provided between the flexible wedge filter 38 and the examinee P.

Figure 4:
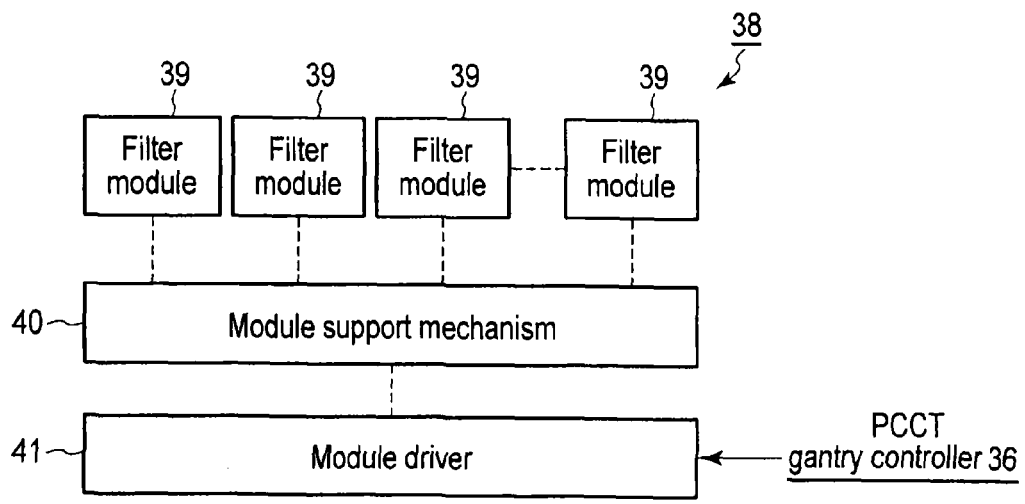
FIG. 4 is a diagram illustrating a configuration of a flexible wedge filter of FIG. 3.

FIG. 4 is a diagram illustrating a configuration of the flexible filter 38. As illustrated in FIG. 4, the flexible filter 38 includes a plurality of filter modules 39, a module support mechanism 40, and a module driver 41. Each of filter modules 39 includes an X-ray shielding material and is configured to individually change an X-ray transmission path length in the X-ray shielding material. The module support mechanism 40 individually operably supports a plurality of filter modules 39. The module driver 41 is a power generating source such as a motor embedded in the module support mechanism 40. The module driver 41 generates power for operating each filter module 39 in response to control of the PCCT gantry controller 36 to operate each filter module 39. The PCCT gantry controller 36 controls the module driver 41 to individually operate filter modules 39 such that an X-ray dose according to the X-ray incident to the X-ray detector 33 from the X-ray 32 tube via the examinee P is distributed substantially uniformly in spatial. More specifically, the PCCT gantry controller 36 controls the module driver 41 depending on the filter shape computed by the filter shape computing unit 54 described below to individually operate a plurality of filter modules 39. The flexible wedge filter 38 will be described in detail below.

As illustrated in FIG. 3, the X-ray detector 33 detects the X-ray generated from the X-ray tube 32. A plurality of detection elements arranged two-dimensionally are mounted on the X-ray detector 33. For example, detection elements are arrayed along an arc centered at the rotation axis Z2 of the rotary frame 31. The arrangement direction of the detection elements along the arc is referred to as a "channel direction." A plurality of detection elements arrayed along the channel direction are referred to as a detection element row. A plurality of detection element rows are arrayed along a row direction with respect to the rotation axis Z2. Each detection element detects an X-ray photon from the X-ray tube 32 and generates an electric pulse (electric signal) depending on the energy of the detected X-ray photon. The detection element includes, for example, a semiconductor diode having electrodes installed in both ends of a semiconductor. The X-ray photon incident to the semiconductor is converted to an electron-hole pair. The number of electron-hole pairs generated by a single incident X-ray photon depends on the energy of the incident X-ray photon. The electron-hole pair is attracted to the electrode. The electrode generates an electric pulse having a peak value corresponding to an electric charge for each electron-hole pair. The electric charge caused by the electron-hole pair is accumulated only for a very short time, for example, corresponding to a standard incident time interval of the X-ray photon. After the accumulation time, the accumulated electric charges are read by the PCCT data acquisition unit 42 from each detection element as an electric pulse (electric signal). The single read electric signal has a peak value corresponding to the energy of the incident X-ray photon. The semiconductor material according to the present embodiment may include a material capable of efficiently converting an X-ray photon into an electron-hole pair with a relatively high atomic number. As a semiconductor material suitable for the PCCT, there are known, for example, CdTe, CdZnTe, and the like.

The PCCT data acquisition unit 42 reads an electric signal using an X-ray detector 33 under control of the PCCT gantry controller 36 and acquires the read electric signal for each view in the PCCT mode. That is, the PCCT data acquisition unit 42 reads the electric signal from the X-ray detector 33 at a timing following a view switching cycle. The PCCT data acquisition unit 42 generates raw data that represents a count of the X-ray photons detected by the X-ray detector 33 for each of a plurality of energy bands (hereinafter, referred to as an "energy bin") included in the energy spectrum of the X-ray photon generated from the X-ray tube 32 based on the electric signal from the X-ray detector 15. Hereinafter, the raw data representing the count of the X-ray photons will be referred to as "count data." The energy bin is set in advance depending on an instruction set by a user using a operation unit 57. The count data is supplied to the console 7 through a contactless type transmitter 43.

Figure 5:
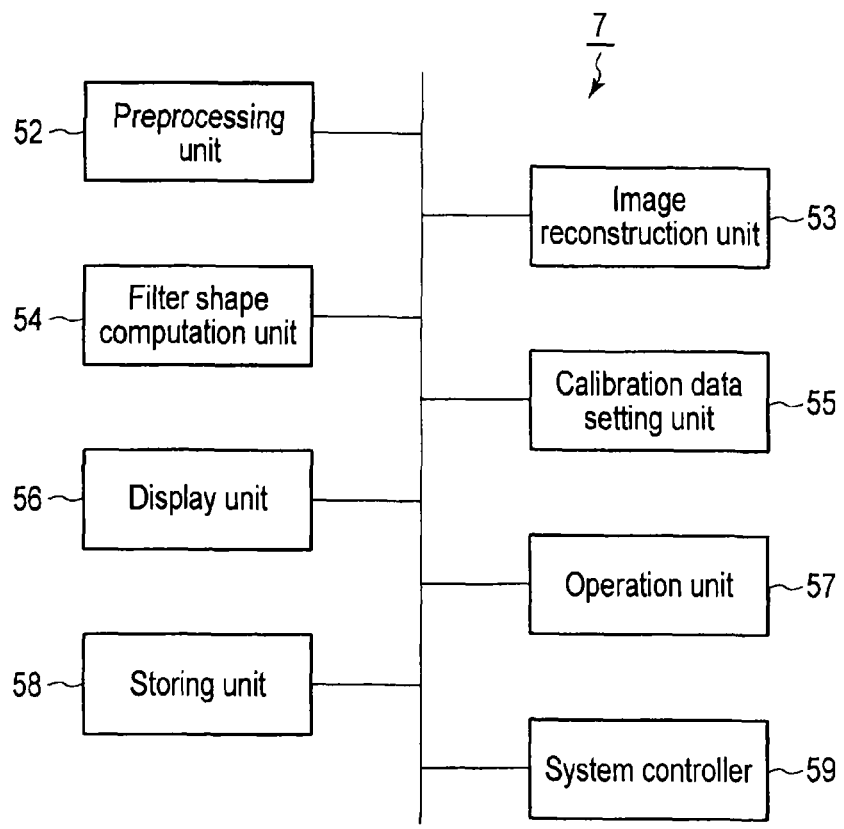
FIG. 5 is a diagram illustrating a configuration of a console of FIG. 1.

FIG. 5 is a diagram illustrating a configuration of the console 7 according to the present embodiment. As illustrated in FIG. 5, the console 7 includes a preprocessing unit 52, an image reconstruction unit 53, a filter shape computing unit 54, a calibration data setting unit 55, a display unit 56, an operation unit 57, and a storing unit 58 in addition to the system controller 51 as a central unit.

The preprocessing unit 52 performs a preprocessing for the CT raw data to generate projection data as input data of the image reconstruction process. The projection data based on the CT raw data will be referred to as "CT projection data." In addition, the preprocessing unit 52 performs a preprocessing for the count data for a plurality of energy bins to generate projection data for a plurality of energy bins. Hereinafter, the projection data based on the count data will be referred to as "PCCT projection data." The CT projection data and the PCCT projection data are supplied to the storing unit 58 for each view. The preprocessing relating to the CT imaging includes, for example, logarithmic transformation and calibration. The preprocessing relating to the PCCT imaging may include a weighted summing of the count data included in the imaging target energy bin for each view. An energy integral value of the X-ray photons included in the imaging target energy bin is computed from the count data through the weighted summing process. Data of the energy integral value is treated substantially equally to the CT raw data. The logarithmic transformation and the calibration are performed for the data of the energy integral value. In the calibration, the calibration data set by the calibration data setting unit 55 is used. As a preprocessing for the PCCT, the imaging target energy bin can be set arbitrarily using the operation unit 57.

The image reconstruction unit 53 applies an image reconstruction process to the CT projection data to generate CT image data for an examinee. In addition, the image reconstruction unit 53 applies an image reconstruction process to the PCCT projection data included in the imaging target energy bin to generate PCCT image data for an examinee from the PCCT projection data. As an image reconstruction algorithm, existing algorithms may be employed, including an analytic image reconstruction method such as a filtered back projection (FBP) or an iterative approximation image reconstruction such as a maximum likelihood expectation maximization (ML-EM) or an ordered subset expectation maximization (OS-EM).

The filter shape computing unit 54 computes a shape of the flexible wedge filter 38 for each predetermined view based on a reference dose distribution. The reference dose distribution is, for example, an incident dose distribution according to an X-ray that transmits the fixed wedge filter 18 and an examinee and is detected by the X-ray detector 13. In addition, the reference dose distribution may be an incident dose distribution according to an X-ray that transmits an examinee in no presence of the fixed wedge filter 18. The shape of the flexible wedge filter 38 is defined by the arrangement of a plurality of filter modules 40. The filter shape computing unit 54 computes a shape of the flexible wedge filter 38, that is, the arrangement of a plurality of filter modules 40 such that a spatial distribution of the dose according to an X-ray after transmitting through an examinee is substantially uniform in a spatial sense. The process in the filter shape computing unit 54 will be described in detail below.

The calibration data setting unit 55 sets calibration data for performing calibration. The calibration is performed to remove attenuation of an X-ray caused by the flexible wedge filter 38 from the PCCT projection data. The calibration data for the CT projection data is set based on the incident dose distribution according to an X-ray that transmits the fixed wedge filter 18 in no presence of the examinee P and reaches to X-ray detector 13. In addition, the calibration data for the PCCT projection data is set based on the incident distribution according to an X-ray that transmits the fixed wedge filter 18 in no presence of the examinee P and reaches to X-ray detector 33. The incident dose distribution is defined by the spatial distribution according to the X-ray incident to the X-ray detector 13 or 33. The process in the calibration data setting unit 55 will be described in detail below.

The display unit 56 displays various types of information such as a CT image or a PCCT image on a display device. The display device may include, for example, a cathode ray tube (CRT) display, a liquid crystal display (LCD), an organic electroluminescent (EL) display, a plasma display.

The operation unit 57 receives various commands or information input from a user through an input device. The input device may include a keyboard, a mouse, a switch, and the like.

The storing unit 58 stores various data such as projection data, a CT image, a PCCT image, and calibration data. In addition, the storing unit 58 stores a control program of the X-ray computed tomography apparatus 1. This control program is to execute a control function for performing the PCCT imaging using the flexible wedge filter 38 in the system controller 51.

The system controller 51 serves as a center of the X-ray computed tomography apparatus 1. Specifically, the system controller 51 reads a control program stored in the storing unit 58 and deploys it on a memory so that each part of the X-ray computed tomography apparatus 1 is controlled based on the deployed control program.

In the X-ray computed tomography apparatus 1 according to the present embodiment, in order to reduce a dynamic range of the PCCT imaging, an incident dose distribution according to an X-ray arrived at the X-ray detector 33 in the presence of an examinee is substantially uniformized by individually operating a plurality of filter modules 39 included in the flexible wedge filter 38. In addition, according to the present embodiment, the dose refers to an integral value of the energy of the incident X-ray photon per unit time. The unit time is defined as, for example, a single view period, a CT imaging period, a PCCT imaging period, and the like.

Hereinafter, the flexible wedge filter 38 mounted on the PCCT gantry 5 and the PCCT imaging using the flexible wedge filter 38 will be sequentially described.

FIG. 6 is a diagram illustrating a simplified configuration of the CT gantry 3 having the fixed wedge filter 18 and an incident dose distribution. As illustrated in FIG. 6, in the CT gantry 3, the fixed wedge filter 18 is provided between the X-ray tube 12 and an examinee P. The X-ray irradiated from the X-ray tube 12 transmits through the fixed wedge filter 18, the slit, and the examinee P and arrives at the detection element of the X-ray detector 13. Here, a direction from the X-ray tube 12 (more specifically, focal point of the X-ray) to the incident detection element will be referred to as an "X-ray path direction." The fixed wedge filter 18 is an X-ray shielding material fabricated such that a thickness increases from the center to the end along the channel direction. The incident dose distribution in the presence of the fixed wedge filter 18 and an examinee P spans across a wide dose range from a high dose to a low dose.

Figure 7:
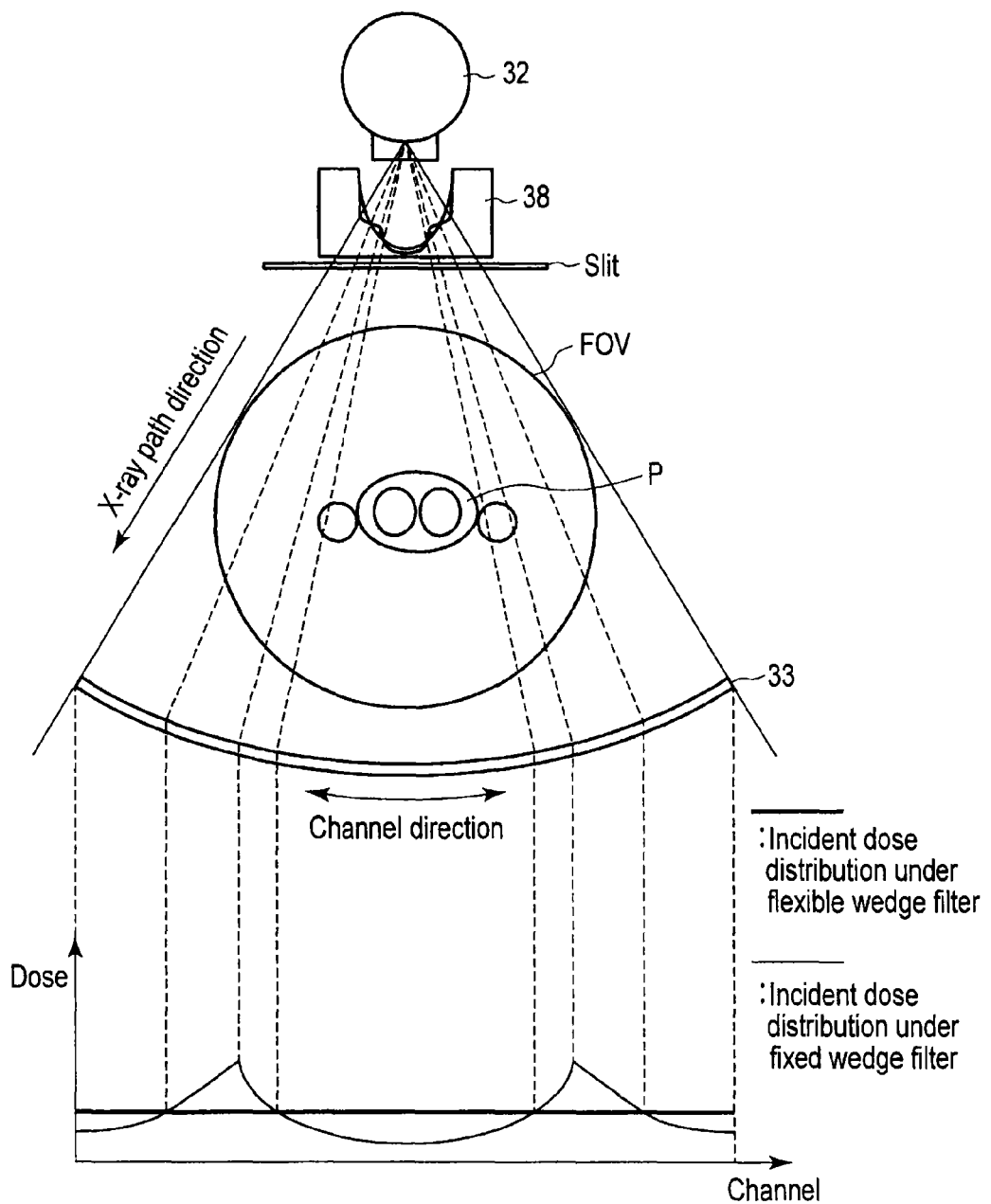
FIG. 7 is a diagram illustrating a simplified configuration of the PCCT gantry having the flexible wedge filter of FIG. 3 and an incident dose distribution.

FIG. 7 is a diagram illustrating a simplified configuration of the PCCT gantry 5 having the flexible wedge filter 38 and an incident dose distribution. As illustrated in FIG. 7, in the PCCT gantry 5, the flexible wedge filter 38 is provided between the X-ray tube 32 and an examinee P. The X-ray irradiated from the X-ray tube 32 transmits through the flexible wedge filter 38, the slit, and the examinee P and arrives at the detection element of the X-ray detector 33. As described above, the flexible wedge filter 38 can at least change an X-ray transmission path length along the channel direction and substantially uniformize the dose according to an X-ray incident to the X-ray detector 33 through the examinee P in a spatial sense. The dynamic range can be reduced by narrowing a range of the dose value of the incident dose. The dose according to an X-ray incident to the X-ray detector 33 in the presence of the flexible filter 38 and an examinee P may be set to a vicinity of the upper limit of the dose rate capable of acquiring data in order to improve a spatial resolution.

Figure 8:
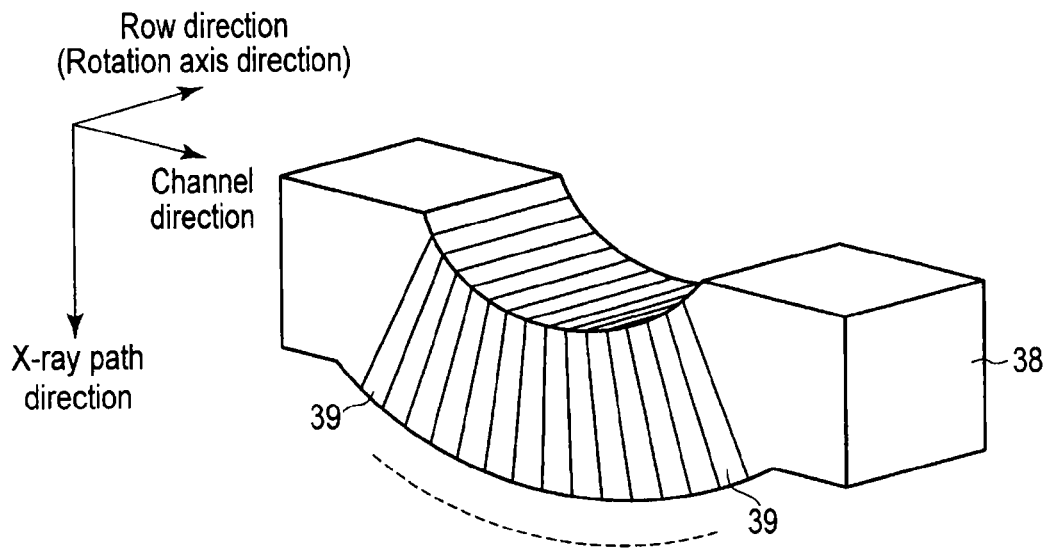
FIG. 8 is a schematic perspective view illustrating the flexible wedge filter of FIG. 3.
Figure 9:
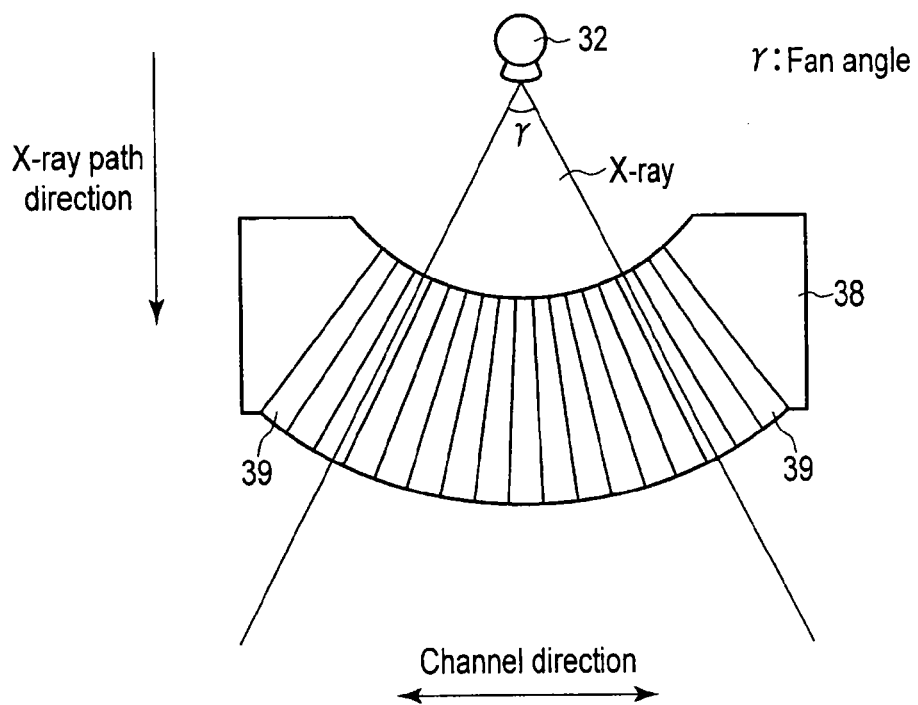
FIG. 9 is a plan view illustrating the flexible wedge filter of FIG. 8 as seen in a row direction.

FIG. 8 is a schematic perspective view illustrating the flexible wedge filter 38, and FIG. 9 is a plan view illustrating the flexible wedge filter 38 as seen in a row direction. As illustrated in FIGS. 8 and 9, the flexible wedge filter 38 has a plurality of filter modules arrange along a direction of a dose uniformization target. The direction of the dose uniformization target is defined as the channel direction in the case of FIGS. 7, 8, and 9. As illustrated in FIG. 9, the filter modules may be arranged in an arc shape or in parallel. When the filter modules are arranged in an arc shape, it is necessary to design a thickness of each filter module 39 in the channel direction so as to be thinner in the X-ray tube 32 side and be thicker in the examinee P side. It should be noted that the arrangement direction of the filter modules 39, that is, the direction of the dose uniformization target is not limited to the channel direction, but may be set to the row direction. In addition, for simplicity purposes, it is assumed that the direction of the dose uniformization target is set to the channel direction unless specified otherwise.

Next, a configuration of the filter module 39 will be described. FIG. 10 is a schematic perspective view illustrating the filter module 39. As illustrated in FIG. 10, the filter module 39 has a pair of wedge-like filters (hereinafter, referred to as a "wedge filter") 391. A pair of wedge filters 391 have substantially the same shape and volume. A pair of wedge filters 391 are supported by a module support mechanism (not illustrated) such that the slope surfaces of the wedges face each other. A long side surface of one of the wedge filters 391 is set as an X-ray incident surface, and a long side surface of the other wedge filter 391 is set as an X-ray output surface. A pair of wedge filters 391 are supported by the module support mechanism (not illustrate) such that the X-ray incident surface and the X-ray output surface are in parallel with each other. If the wedge filters 391 are arranged in this manner, the X-ray transmission path lengths through the filter modules 39 are substantially equalized irrespective of the row direction. The wedge filter 391 includes an X-ray shielding material for attenuating the dose. A material of the wedge filter 391 may include any material capable of attenuating the dose, such as aluminum, metal, and plastic.

In order to make the X-ray transmission path length in the filter module 39 changeable, the module support mechanism 40 supports a pair of wedge filters 391 such that the pair of wedge filters 391 can individually slide along a direction perpendicular to the arrangement direction (channel direction) and the X-ray path direction, that is, along the row direction. In other words, the module support mechanism 40 supports a pair wedge filters 391 such that they can approach or recede from each other along the row direction. A pair of wedge filters 391 slide by the module driver 41 oppositely in the row direction.

Figure 11:
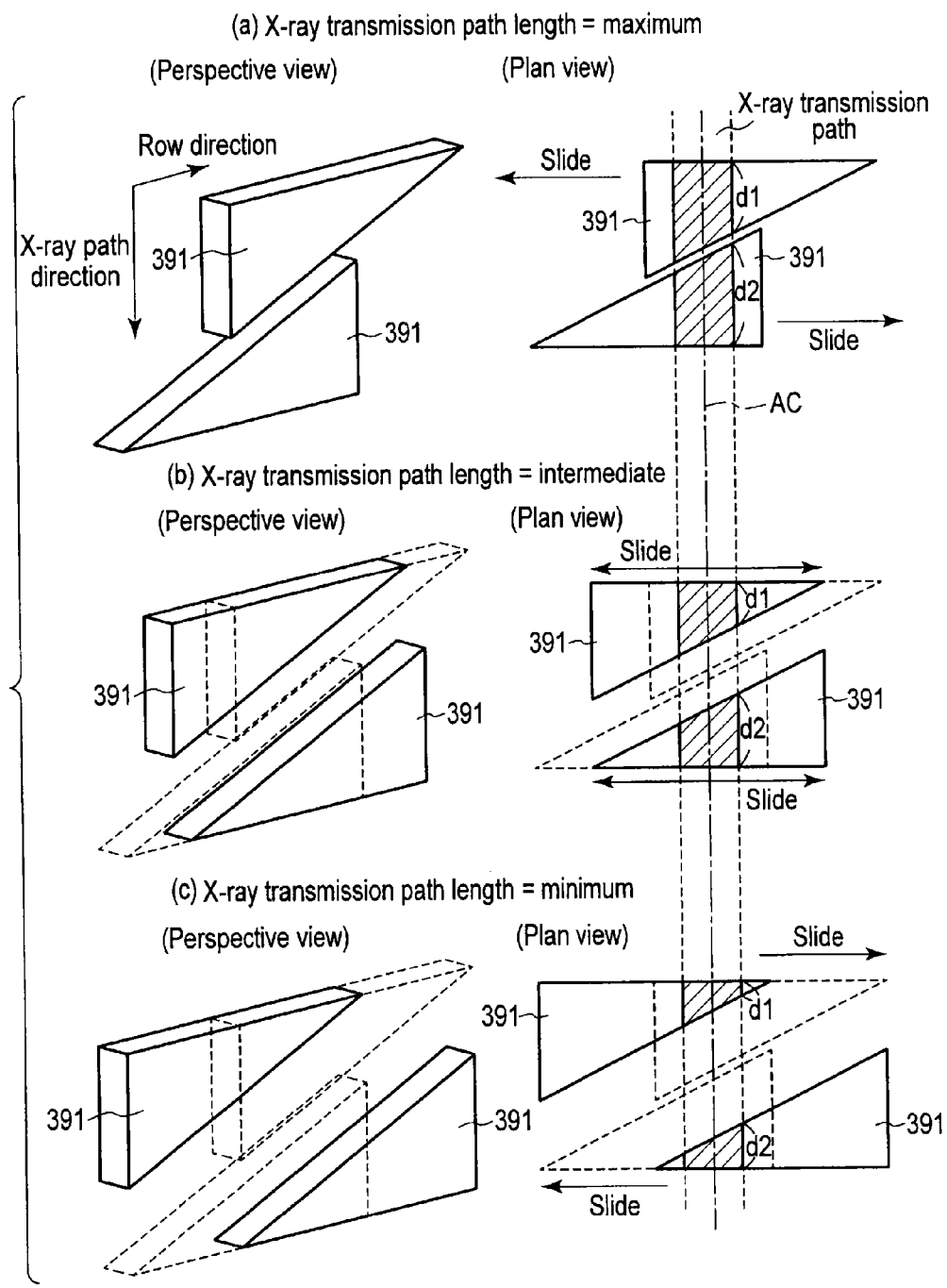
FIG. 11 is a diagram for describing an operation of changing an X-ray transmission path length by sliding a pair of wedge filters of FIG. 10.

FIG. 11 is diagram for describing an operation of changing the X-ray transmission path length by sliding a pair of wedge filters 391. FIG. 11 (a) illustrates an exemplary arrangement of a pair of wedge filters 391 in a case where the X-ray transmission path length is at maximum. FIG. 11 (b) illustrates an exemplary arrangement of a pair of wedge filters 391 in a case where the X-ray transmission path length is intermediate. FIG. 11 (c) illustrates an exemplary arrangement of a pair of wedge filters 391 in a case where the X-ray transmission path length is at minimum. In each of FIGS. 11 (a), (b), and (c), a perspective view and a plan view of a pair of wedge filters 391 are illustrated. The X-ray has a predetermined width with respect to the center axis AC of the X-ray transmission path in the row direction. A total distance in the X-ray path direction of the area where the X-ray transmission path intersects with a pair of wedge filters 391 (hatching area in FIGS. 11 (a), (b), and (c)) is defined as the X-ray transmission path length. That is, a sum of the distance d1 in the X-ray path direction of the area where the X-ray transmission path intersects with the upper wedge filter 391 and the distance d2 in the X-ray path direction of the area where the X-ray transmission path intersects with the lower wedge filter 391 is defined as the X-ray transmission path length. The X-ray transmission path length changes depending on a gap distance in the row direction between a pair of the wedge filters. As the gap distance is shortened, the X-ray transmission path length is lengthened. Conversely, as the gap distance is lengthened, the X-ray transmission path length is shortened. A changeable width of the X-ray transmission path length can be designed arbitrarily depending on an angle of the slope surface of the wedge filter 391 and the slidable distance. In addition, the changeable width of the X-ray transmission path length may be set such that the X-ray passes through a pair of the wedge filters 391 when the X-ray transmission path length is either at maximum or at minimum.

Next, the PCCT imaging using the flexible wedge filter will be described.

Figure 12:
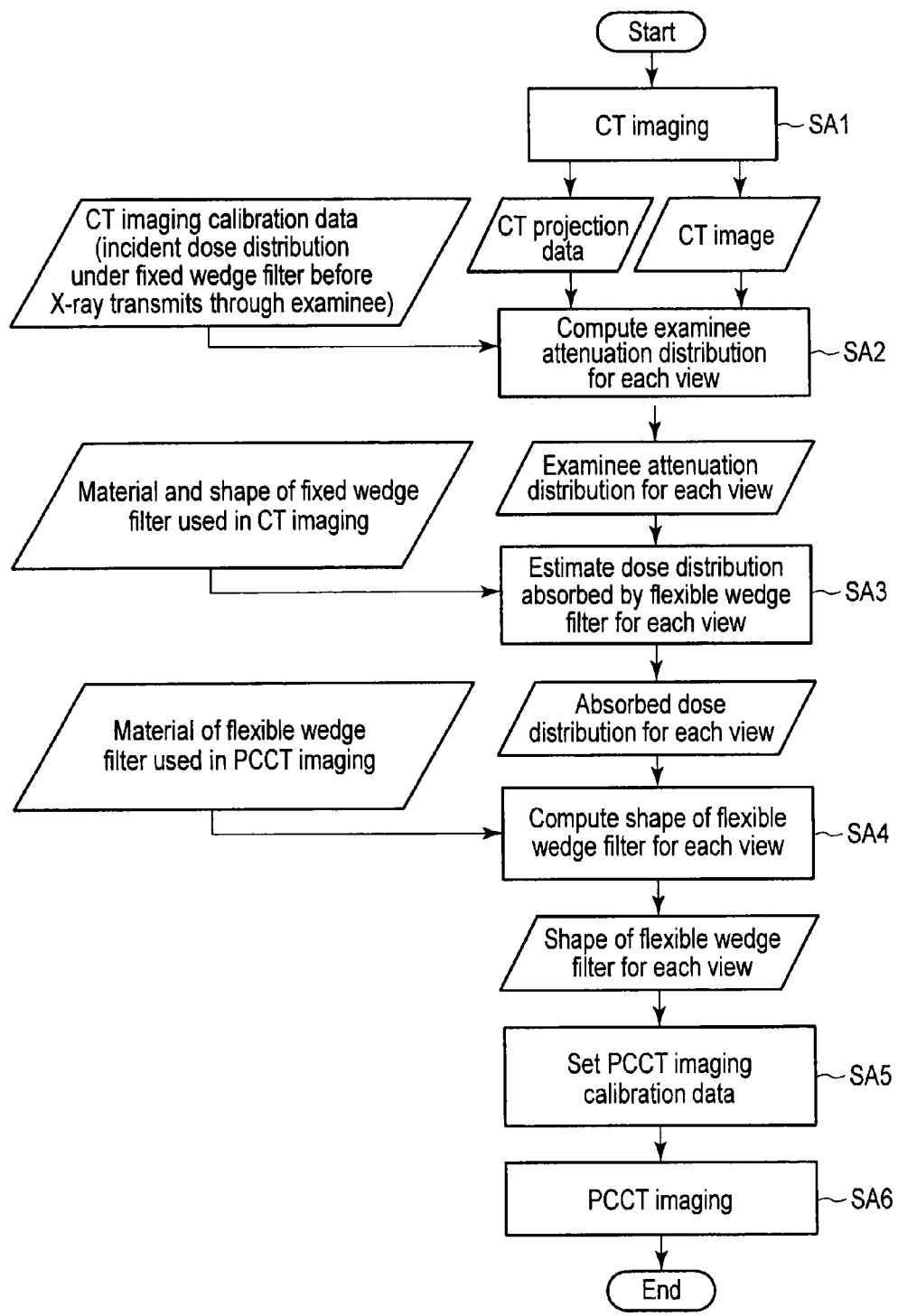
FIG. 12 is a diagram illustrating a typical flow of the operation in the X-ray computed tomography apparatus performed under control of the system controller of FIG. 5.

FIG. 12 is a diagram illustrating a typical flow of the operation of the X-ray computed tomography apparatus 1 performed under control of the system controller 51. As illustrated in FIG. 12, according to the present embodiment, both the CT imaging and the PCCT imaging are performed. The CT imaging is performed to acquire data for controlling the flexible wedge filter 38, that is, data about the shape of the flexible wedge filter. The PCCT imaging is performed by controlling the flexible wedge filter 38 using the control data acquired through the CT imaging.

As illustrated in FIG. 12, as the CT imaging is prepared, a user inputs a CT imaging start instruction using the operation unit 57. As the CT imaging start instruction is input, the system controller 51 controls the CT gantry controller 16 in the CT gantry 3 to perform the CT imaging for an examinee P (step SA1). When the CT imaging is only to acquire the data about the shape of the flexible wedge filter, the imaging may be performed at a significantly low resolution and a significantly low dose. When the CT imaging is performed to acquire the CT image for photographic diagnosis as well as acquisition of the data about the shape of the flexible wedge filter, the CT imaging may be performed at a typical resolution and a typical dose.

In the CT imaging, the CT gantry controller 16 controls the rotary driver 15 to rotate the rotary frame 11, the high-voltage generator 17 to generate an X-ray from the X-ray tube 12, and the CT data acquisition unit 19 to acquire the CT raw data for each view. The CT raw data is supplied to the console 7 and is stored in the storing unit 58. The preprocessing unit 52 performs the preprocessing for the CT raw data of each view to generate the CT projection data of each view. The image reconstruction unit 53 generates CT image data based on the CT projection data for a plurality of views. The CT raw data represents an incident dose distribution after an X-ray transmits through the fixed wedge filter 18 and an examinee P. The CT projection data represents a spatial distribution of logarithmic transformation of the dose after an X-ray transmits through the fixed wedge filter 18 and an examinee P. The spatial distribution means a distribution in the channel direction. The CT projection data and the CT image of each view are stored in the storing unit 58.

As the CT imaging is performed, the system controller 51 causes the filter shape computing unit 54 to execute a process of computing the transmission dose distribution (step SA2). In step SA2, the filter shape computing unit 54 computes an examinee attenuation distribution for each view based on the CT imaging calibration data and the CT projection data or the CT image data. The examinee attenuation distribution represents a distribution of the dose value attenuated by an examinee P in the channel direction. The CT imaging calibration data represents an incident dose distribution in no presence of the fixed wedge filter 18 and an examinee.

Figure 13:
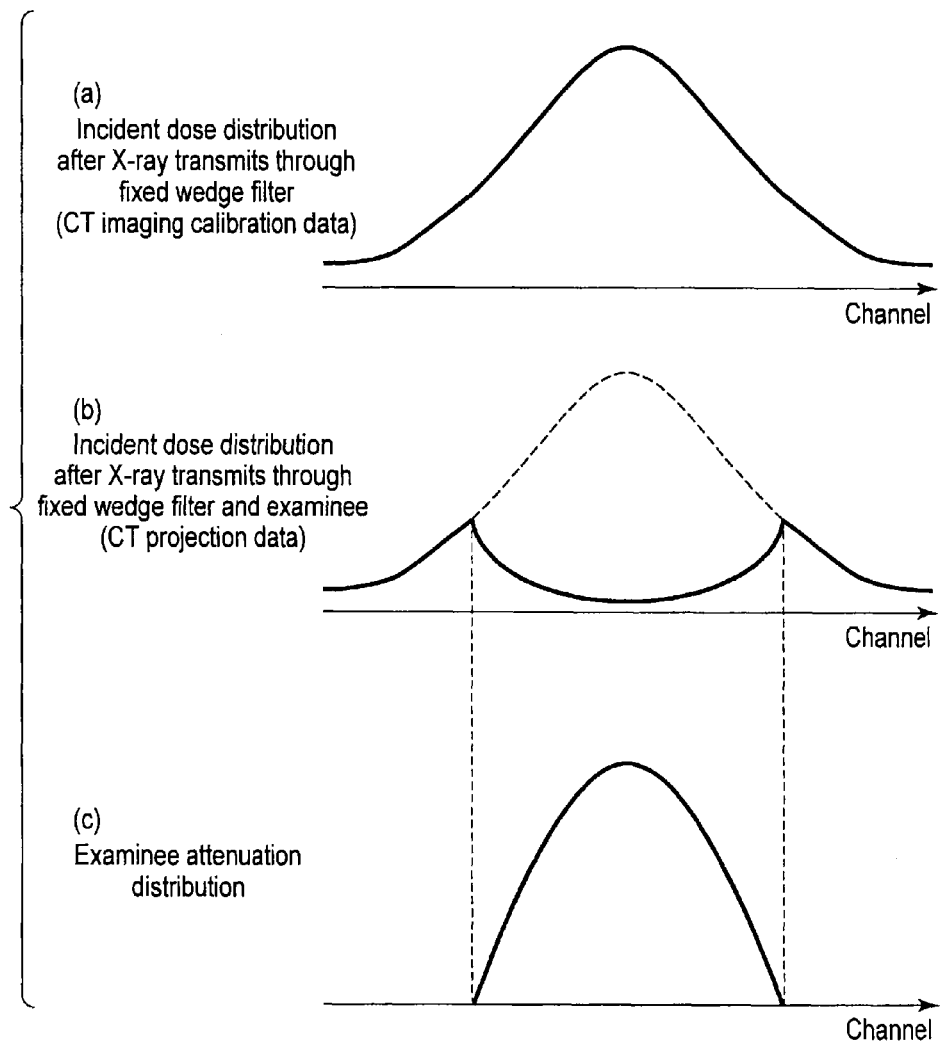
FIG. 13 is a diagram for describing a method of computing an examinee attenuation distribution using CT imaging calibration data and CT projection data in step SA2 of FIG. 12.

FIG. 13 is diagram for describing a method of computing the examinee attenuation distribution using the CT imaging calibration data and the CT projection data. FIG. 13 (a) illustrates the CT imaging calibration data, that is, an incident dose distribution in no presence of the fixed wedge filter 18 and an examinee. FIG. 13 (b) illustrates the CT projection data, that is, an incident dose distribution after an X-ray transmits through the fixed wedge filter 18 and an examinee. FIG. 13 (c) illustrates the examinee attenuation distribution. As illustrated in FIGS. 13 (a), (b), and (c), the examinee attenuation distribution is equal to the difference between the calibration data and the CT projection data. The filter shape computing unit 54 computes the examinee attenuation distribution by subtracting the CT projection data from the calibration data. The examinee attenuation distribution is computed for each view. The examinee attenuation distribution is stored in the storing unit 58 for each view.

As step SA2 is performed, the system controller 51 causes the filter shape computing unit 54 to execute a process of computing the absorbed dose distribution (step SA3). In step SA3, the filter shape computing unit 54 computes the absorbed dose distribution of each view using the material and the shape of the fixed wedge filter 18 used for the CT imaging from the examinee attenuation distribution. Specifically, the shape of the fixed wedge filter 18 is defined by the X-ray transmission path length of each X-ray path in the fixed wedge filter 18. The absorbed dose distribution is a distribution of the absorbed dose value in the channel direction. The absorbed dose value is defined by the dose value according to the X-ray absorbed by the flexible wedge filter 38 in the PCCT imaging. In the PCCT imaging, due to reduction of a dynamic range or the like, it is preferable that the dose according to the X-ray incident to the X-ray detector 13 be substantially uniform in the channel direction. That is, the absorbed dose value is defined as a value obtained by subtracting a target dose value from the incident dose value after the X-ray transmits through only an examinee. The target dose value is a target value of the incident dose in the PCCT imaging. The target dose value has a substantially uniform value in the channel direction. The target dose value may be set to a highest possible value under a condition that no overflow is generated from the viewpoint of improvement of a spatial resolution. The target dose value may be set to an arbitrary value by a user using the operation unit 56. The absorbed dose distribution is stored in the storing unit 58 for each view.

As step SA3 is performed, the system controller 51 causes the filter shape computing unit 54 to execute a process of computing the filter shape (step SA4). In step SA4, the filter shape computing unit 54 computes the shape of the flexible wedge filter of each view using a material of the flexible wedge filter 38 used in the PCCT imaging from the absorbed dose distribution of each view. More specifically, first, for each filter module 39 of the flexible wedge filter 38, the filter shape computing unit 54 computes the X-ray transmission path length for setting the incident dose value to the target dose value for each view using a material of the flexible wedge filter 38 from the absorbed dose distribution. Then, the filter shape computing unit 54 computes an arrangement of the wedge filters 391 for each view based on the X-ray transmission path length. As described above, there is a matching relationship between the X-ray transmission path length and a pair of wedge filters 391. The filter shape computing unit 54 computes the arrangement of the wedge filters 391 in each filter module 39 as shape data of the flexible wedge filter from the X-ray transmission path length based on this matching relationship. The shape data of the flexible wedge filter is stored in the storing unit 58 for each view.

As step SA4 is performed, the system controller 51 causes the calibration data setting unit 55 to perform a setting process (step SA5). In step SA5, the calibration data setting unit 55 sets the calibration data depending on the shape of the flexible filter computed in step SA4 based on various methods. The calibration data is used to extract an attenuation component caused by an examinee P from the PCCT projection data.

As a method of setting the calibration data, for example, the calibration data may be directly measured using the flexible wedge filter 38 set in practice. Alternatively, the closest one may be selected from distribution data of various shapes acquired in advance. Alternatively, a distribution shape may be obtained by computing data of the corresponding detection element by interpolating the data measured at a plurality of X-ray transmission path lengths for each filter module 39 of the flexible wedge filter 38. The calibration data is stored in the storing unit 58 for each view.

As step SA5 is performed, the system controller 51 waits for the PCCT imaging start instruction. As the PCCT imaging is prepared, a user inputs the PCCT imaging start instruction using the operation unit 56.

As the PCCT imaging start instruction is input, the system controller 51 controls the PCCT gantry controller 36 in the PCCT gantry 5 to perform the PCCT imaging for an examinee P (step SA6). In step SA6, the PCCT gantry controller 36 controls the rotary driver 35 to rotate the rotary frame 31, controls the high-voltage generator 37 to generate an X-ray from the X-ray tube 32, and controls the PCCT data acquisition unit 42 to acquire the count data for a plurality energy bins for each view. In this case, the PCCT gantry controller 36 controls the module driver 41 for each view such that the filter modules 39 are arranged according to the shape data of the flexible wedge filter. The module driver 41 makes a pair of wedge filters 391 for each of the filter modules 39 in response to the control from the PCCT gantry controller 36 to move the wedge filters 391 to match the arrangement corresponding to the shape of the flexible wedge filter. As a result, the dose incident to the X-ray detector 33 is substantially uniformly distributed in the channel direction.

FIG. 14 illustrates control of the distribution of the X-ray transmission path length in the channel direction using the flexible wedge filter. FIG. 14 (a) is a perspective view illustrating the flexible wedge filter in an exemplary arrangement of a plurality of filter modules. FIG. 14 (b) is a plan view illustrating a plurality of filter modules in the arrangement of FIG. 12 (a). FIG. 14 (c) is a cross-sectional view illustrating the flexible wedge filter in the arrangement of FIG. 14 (a). FIG. 14 (d) illustrates a distribution of the X-ray transmission path length in the arrangement of FIG. 14 (a). The plan view of FIG. 14 (b) is a plan view of the filter module, as seen in the channel direction. The cross-sectional view of FIG. 14 (c) is a cross-sectional view for the cross section defined in the channel direction and the X-ray path direction. The hatching portion of FIG. 14 (c) indicates the area occupied by the wedge filter 391, and the blank portion indicates a space where no wedge filter 391 exists. As illustrated in FIGS. 14 (a), (b), (c), and (d), the X-ray transmission path length in the X-ray path direction changes depending on the distance in the row direction between a pair of wedge filters 391. It is possible to change the dose distribution in the channel direction by changing the X-ray transmission path length. The PCCT gantry controller 36 controls the module driver 41 for each view according to the shape of the flexible wedge filter such that the arrangement of the filter module is implemented depending on the shape of the flexible wedge filter for each view. In order to shorten the X-ray transmission path length from the center to the edge in the channel direction, a distance between a pair of wedge filters 391 in the channel direction is set to increase from the center to the edge in the channel direction.

The count data relating to a plurality of energy bins acquired by the PCCT data acquisition unit 42 is supplied to the console 7 via the transmitter 43 and is stored in the storing unit 58. The preprocessing unit 52 performs a preprocessing for the count data relating to a plurality of energy bins to generate PCCT projection data relating to a plurality of energy bins. In the preprocessing, calibration using the calibration data is performed.

Figure 15:
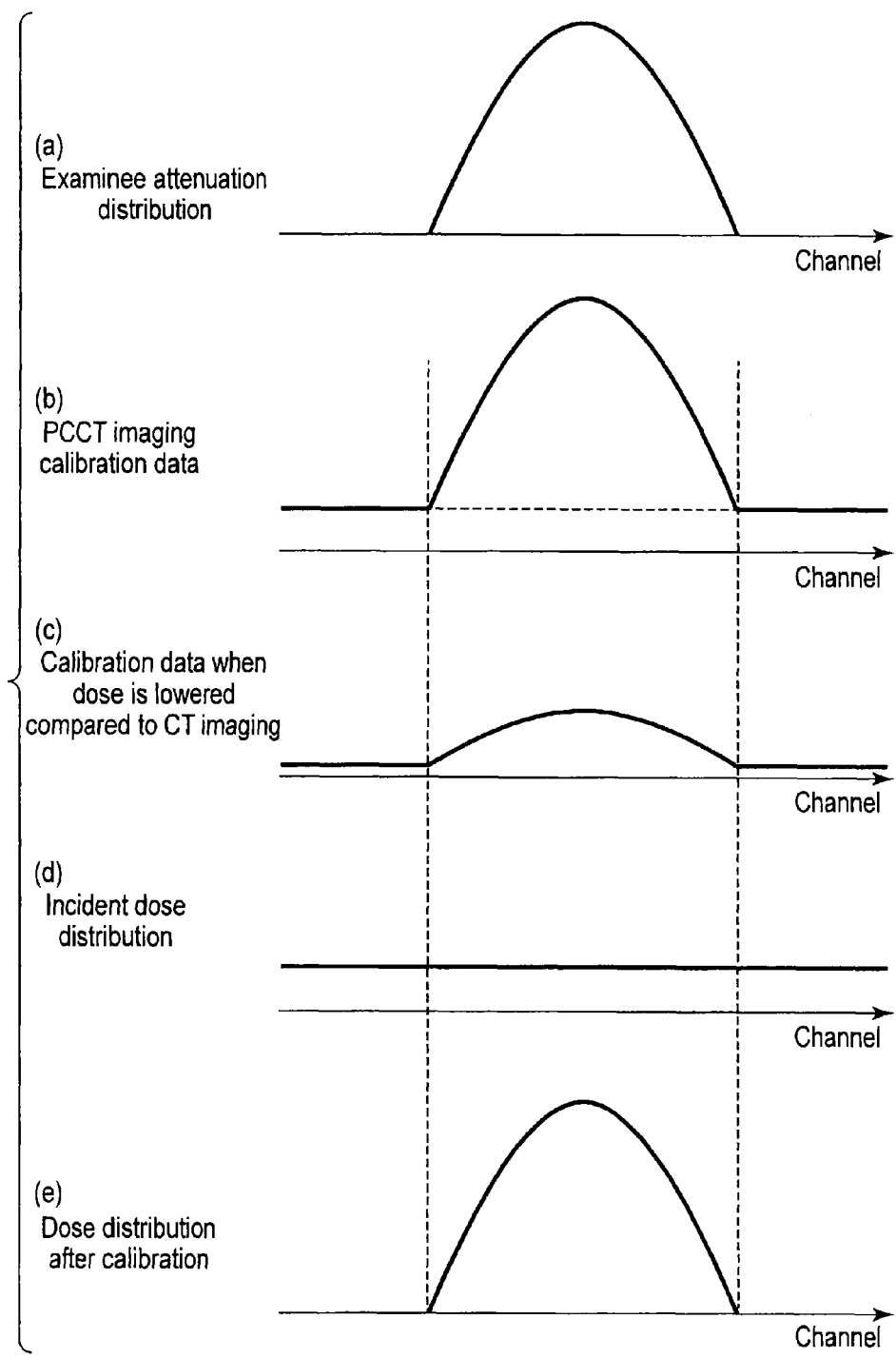
FIG. 15 is a diagram illustrating a dose distribution in PCCT imaging performed in step SA5 of FIG. 12.

FIG. 15 is diagrams illustrating a dose distribution in the PCCT imaging according to the present embodiment. FIG. 15 (a) illustrates the examinee attenuation distribution. FIG. 15 (b) illustrates the PCCT imaging calibration data. FIG. 15 (c) illustrates the calibration data when the dose is lowered compared to the CT imaging. FIG. 15 (d) illustrates the incident dose distribution. FIG. 15 (e) illustrates the dose distribution after the calibration. The examinee attenuation distribution is computed based on the CT imaging calibration data of step SA2 and the CT projection data or the CT image data. A result of adding the dose distribution uniform in the channel direction to the examinee attenuation distribution is set to the calibration data by the calibration data setting unit 55. In the PCCT imaging, the dose rate is lowered such that an overflow is not easily generated. The shape of the dose distribution is maintained even when the dose rate is lowered. Therefore, the calibration setting unit 55 may compute the PCCT imaging calibration data based on the dose distribution obtained by adding a certain value to the examinee attenuation distribution and a difference between the CT imaging dose and the PCCT imaging dose. For example, the dose distribution of FIG. 15 (c) obtained by lowering the dose of FIG. 15B as a whole may be set as the calibration data. The dose distribution incident to the X-ray detector 33 through the PCCT imaging becomes substantially uniform in the channel direction through the control for the filter module 39 of the flexible wedge filter 38 described above. The preprocessing unit 52 performs calibration for the PCCT projection data based on the dose distribution incident to the X-ray detector 33. In the calibration, the preprocessing unit 52 subtracts the PCCT calibration data from the PCCT projection data. The dose distribution indicated by the PCCT projection data after the subtraction represents a distribution of the dose absorbed by an examinee in the channel direction as illustrated in FIG. 15 (e).

It should be noted that, although FIG. 15 (e) illustrates a single calibrated dose distribution for illustrative purposes, the calibrated dose distribution has a different shape for each energy bin.

The image reconstruction unit 53 generates a PCCT image for an imaging target energy bin based on the PCCT projection data for the imaging target energy bin out of a plurality of energy bins. The PCCT image is displayed on the display unit 57.

Hereinbefore, the PCCT imaging using the flexible wedge filter 38 according to the present embodiment has been described.

It should be noted that, from the viewpoint of accuracy of the dose uniformization, the number of the detection elements where an X-ray transmitting through a single filter module 39 arrives in the channel direction is preferably set to one. However, in a relationship of the volume between the filter module 39 and the detection element, it is conceived that the X-ray transmitting through a single filter module 39 arrives at a plurality of the detection elements. In this case, it is difficult to perfectly uniformize the incident dose value in the channel direction. However, according to the present embodiment, the aim is to reduce the dynamic range of the dose. Therefore, it is not necessary to perfectly uniformize the incident dose value. Unevenness may occur in the incident dose distribution depending on the number of the mounted filter modules using the flexible wedge filter 38.

In addition, in the aforementioned embodiment, the operation of the filter modules 39 is controlled for each view depending on the shape data of the flexible wedge filter. However, the present embodiment is not limited thereto. The operation of the filter modules 39 may be controlled in the unit of two or more views if an uniformization degree of the dose can be reduced. Even in this case, it is possible to reduce the dynamic range of the dose, compared to the prior art.

Modification 1

In the aforementioned description, the filter module 39 is not limited to a configuration including a pair of wedge filters 391. For example, if the minimum X-ray transmission path length is long at some extent, another type of the filter module may be used. Hereinafter, another filter module will be described. In the following description, like reference numerals denote like element as in the filter module, and the description thereof will be repeated only when necessary.

FIG. 16 is a perspective view illustrating another filter module 39'. As illustrated in FIG. 16, another filter module 39' includes a pair of wedge filters 391 and a single fixed filter 392. A pair of wedge filters 391 are movable individually in the channel direction, and the fixed filter 392 is fixedly supported by a module support mechanism 40 (not illustrated). A material of the fixed filter 392 may include any material capable of attenuating the dose, such as aluminum, metal, or plastic. The fixed filter 392 has a constant thickness in the channel direction and the row direction, that is, a constant X-ray transmission path length in the channel direction and the row direction. Under such a geometrical condition of the fixed filter 392, the X-ray transmission path length in the fixed filter 392 becomes constant even when the fixed filter 392 slides in the channel direction or the row direction.

Figure 17:
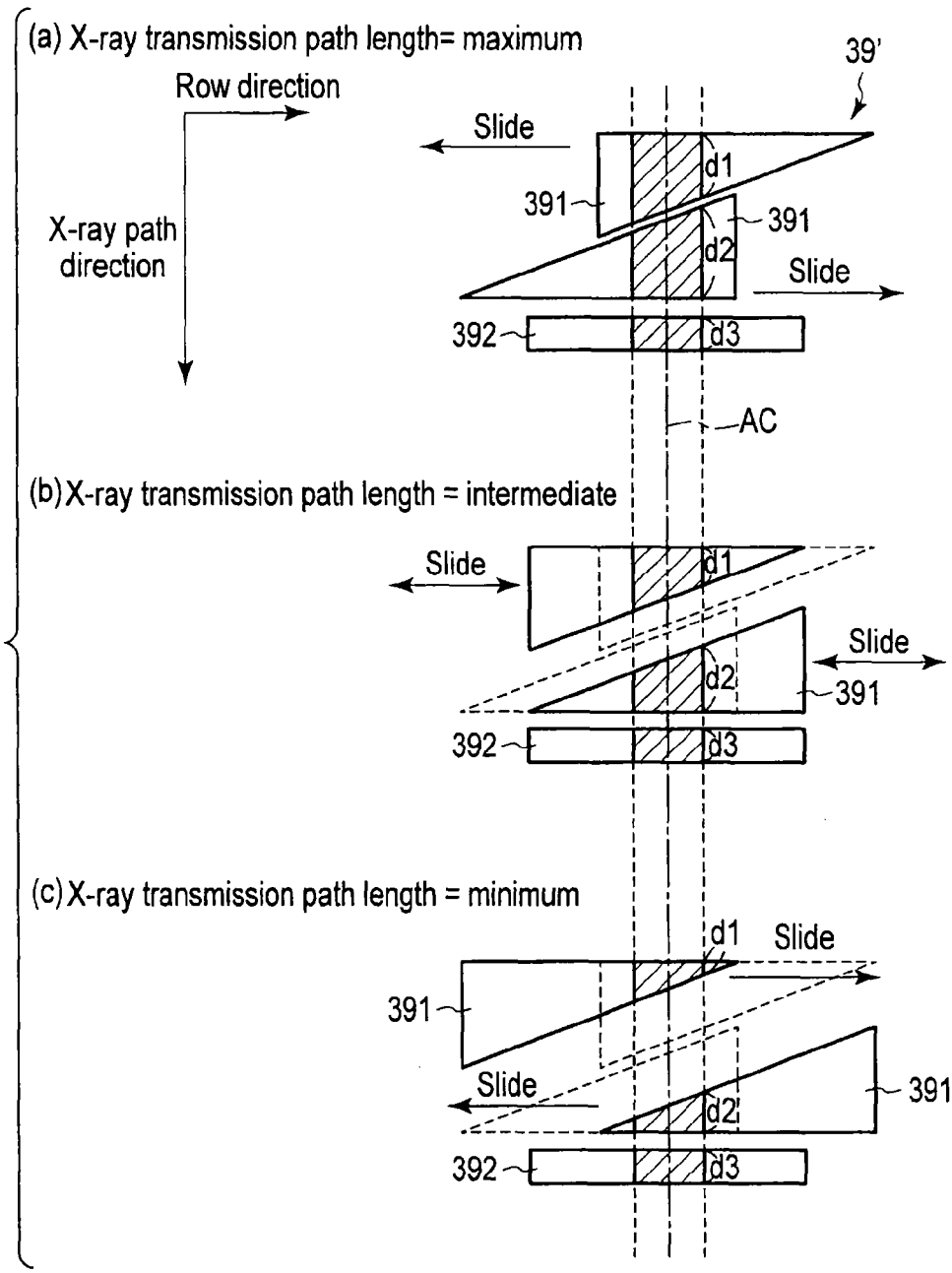
FIG. 17 is a diagram for describing an operation of changing the X-ray transmission path length in another filter module by sliding a pair of wedge filters according to Modification 1.

FIG. 17 is diagram for describing the operation of changing the X-ray transmission path length in another filter module 39' by sliding a pair of wedge filters 391. FIG. 17 (a) illustrates an exemplary arrangement of a pair of wedge filters 391 and a single fixed filter 392 when the X-ray transmission path length is at maximum. FIG. 17 (b) illustrates an exemplary arrangement when the X-ray transmission path length is intermediate. FIG. 17 (c) illustrates an exemplary arrangement when the X-ray transmission path length is at minimum. In each of FIGS. 17 (a), (b), and (c), a plan view of a pair of wedge filters 391 and a single fixed filter 392 is illustrated. The X-ray has a predetermined width with respect to the center axis AC of the X-ray transmission path in the row direction. A total sum of the distance of the area where the X-ray transmission path intersects with the wedge filter 391 and the fixed filter 392 (hatching area in FIGS. 17 (a), (b), and (c)) in the X-ray transmission direction is defined as the X-ray transmission path length. That is, a total sum of a distance d1 of the area where the X-ray transmission path intersects with the upper wedge filter 391 in the X-ray path direction, a distance d2 of the area where the X-ray transmission path intersects with the lower wedge filter 391 in the X-ray path direction, a distance d3 of the area where the X-ray transmission path intersects with the fixed filter 392 in the X-ray path direction is defined as the X-ray transmission path length. The fixed filter 392 may be provided in a case where the minimum X-ray transmission path length has a predetermined length. In order to improve accuracy of the movement control of the wedge filter 391 using the module driver 42, a weight of the filter module 39 may be reduced by employing the fixed filter 392. For example, the weight of the wedge filter 391 may be reduced by designing the angle of the slope surface of the wedge of the wedge filter 391 to be relatively shallow. It should be noted that the fixed filter 392 may be provided in each of the filter modules 39, or a single fixed filter 392 may be provided for a predetermined number of filter modules 39. Alternatively, a single fixed filter may be provided for overall filter modules 39 mounted on the flexible wedge filter 38.

Modification 2

In the aforementioned description, the filter shape computing unit 54 computes the shape of the flexible wedge filter using the CT imaging calibration data. However, a method of computing the shape of the flexible wedge filter is not limited thereto. In the filter shape computing unit 54 according to Modification 2, the shape data of the flexible wedge filter is computed without using the CT imaging calibration data. Hereinafter, computation of the shape data of the flexible wedge filter according to Modification 2 will be described. In the following description, like reference numerals denote like elements as in the present embodiment, and the description thereof will be repeated only when necessary.

Figure 18:
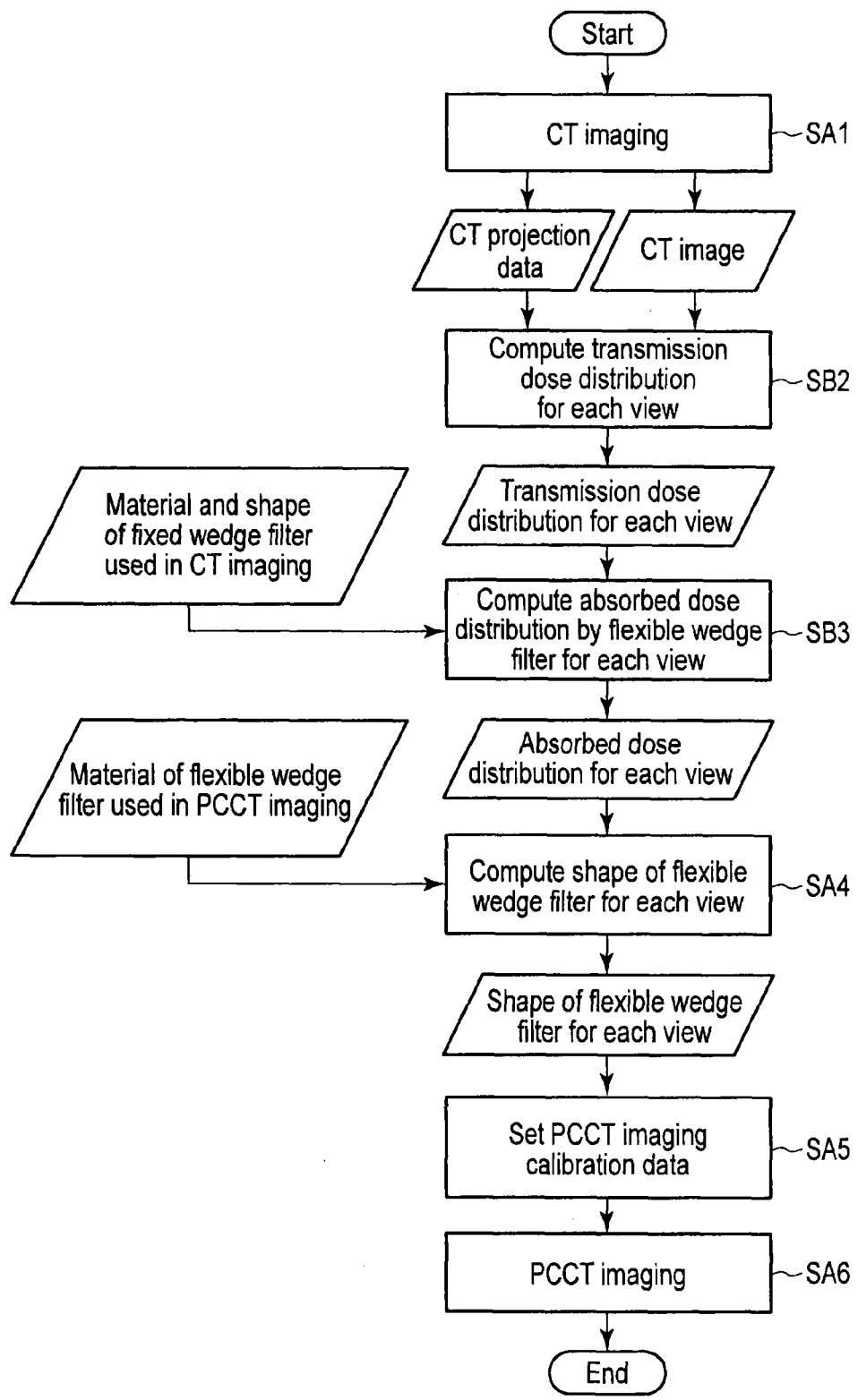
FIG. 18 a diagram illustrating a typical flow of the operation of the X-ray computed tomography apparatus 1 performed under control of the system controller according to Modification 2.

FIG. 18 is a diagram illustrating a typical flow of the operation of the X-ray computed tomography apparatus 1 performed under control of the system controller 51 according to Modification 2.

As illustrated in FIG. 18, as the CT imaging is prepared, a user inputs a CT imaging start instruction using the operation unit 56. As the CT imaging start instruction is input, the system controller 51 controls the CT gantry controller 16 of the CT gantry 3 to perform the CT imaging for an examinee P (step SA1).

As the CT imaging is performed, the system controller 51 causes the filter shape computing unit 54 to execute a process of computing the transmission dose distribution (step SB2). In step SB2, the filter shape computing unit 54 computes the transmission dose distribution of each view based on the CT projection data or the CT image data of each view. The transmission dose distribution represents the dose distribution incident to the X-ray detector 13 after the X-ray transmits through the fixed wedge filter 18 and an examinee P. That is, the transmission dose distribution is substantially equal to a distribution of the output value of each detection element included in the CT raw data. When the dose distribution is computed based on the CT image data, a process such as reprojection is employed.

As step SB2 is performed, the system controller 51 causes the filter shape computing unit 54 to execute a process of computing the absorbed dose distribution (step SB3). In step SB3, the filter shape computing unit 54 computes the absorbed dose distribution of each view using the material and the shape of the fixed wedge filter 18 used in the CT imaging from the transmission dose distribution. The absorbed dose distribution is a distribution of the absorbed dose value in the channel direction. The absorbed dose value is defined by the dose value of the X-ray absorbed by the flexible wedge filter 38 in the PCCT imaging. In the PCCT imaging, in order to reduce the dynamic range, it is preferably that the dose according to X-ray incident to the X-ray detector 13 be substantially uniform in the channel direction. That is, the absorbed dose value is defined as a value obtained by subtracting a target dose value from the transmission dose value. The target dose value is a target value of the incident dose in the PCCT imaging. The target dose value has a substantially uniform value in the channel direction. The target dose value is preferably set to a highest possible value under a condition that no overflow is generated from the viewpoint of improvement of the spatial resolution. The target dose value may be set to an arbitrary value by a user using the operation unit 57. The absorbed dose distribution is stored in the storing unit 58 for each view.

As step SB3 is performed, the system controller 51 causes the filter shape computing unit 54 to execute a process of computing the filter shape (step SB4). In step SB4, the filter shape computing unit 54 computes the shape of the flexible wedge filter of each view using the material of the flexible wedge filter 38 used in the PCCT imaging from the absorbed dose distribution of each view. More specifically, first, for each filter module 39 of the flexible wedge filter 38, the filter shape computing unit 54 computes the X-ray transmission path length for setting the incident dose value as the target dose value for each view using the material of the flexible wedge filter 38 from the absorbed dose. Then, the filter shape computing unit 54 computes the arrangement of the wedge filters 391 for each view based on the X-ray transmission path length. The filter shape computing unit 54 computes the arrangement of the wedge filters 391 in each filter module 39 as the shape data of the flexible wedge filter depending on the matching relationship between a pair of wedge filters 391 and the X-ray transmission path length. The shape of the flexible wedge filter is stored in the storing unit 58 for each view.

As step SA4 is performed, the system controller 51 causes the calibration data setting unit 55 to execute a setting process (step SA5). In step SA5, the calibration data setting unit 55 sets the calibration data depending on the flexible filter shape computed in step SA4 using the method described in the present embodiment.

As step SA5 is performed, the system controller 51 waits for the PCCT imaging start instruction. As the PCCT imaging is prepared, a user inputs the PCCT imaging start instruction using the operation unit 56. As the PCCT imaging start instruction is input, the system controller 51 controls the PCCT gantry controller 36 of the PCCT gantry 5 to perform the PCCT imaging for an examinee P (step SA6).

Hereinbefore, the PCCT imaging using the flexible wedge filter 38 according to Modification 2 has been described.

In this manner, according to Modification 2, it is possible to compute the shape of the flexible wedge filter without using the CT imaging calibration data.

Modification 3

In the aforementioned description, the dose value is uniformized in the channel direction. However, the present embodiment is not limited thereto. That is, the dose value may be uniformized in the row direction. Hereinafter, a flexible wedge filter will be described by assuming that the dose value is uniformized in the row direction. In addition, in the following description, like reference numerals denote like elements as in the present embodiment, and the description thereof will be repeated only when necessary.

FIG. 19 is a schematic perspective view illustrating the flexible wedge filter 39' according to Modification 3. FIG. 20 is a plan view illustrating the flexible wedge filter 38' according to Modification 3 as seen in the row direction. As illustrated in FIGS. 19 and 20, the flexible wedge filter 38' has a plurality of filter modules 39 arranged in a target dose uniformization direction, that is, in the row direction. A plurality of filter modules 39 may be arranged in an arc shape or in parallel with each other as illustrated in FIGS. 19 and 20. When a plurality of filter modules 39 are arranged in an arc shape, it is necessary to perform a design such that a thickness of each filter module 30 in the row direction is thinner in the X-ray tube 32 side and is thicker in an examinee P side.

In this manner, according to Modification 3, it is possible to substantially uniformize the dose value in the row direction. Therefore, it is possible to also reduce the dynamic range in the row direction.

Modification 4

In the aforementioned description, the dose value is uniformized in the channel direction or the row direction. However, the present embodiment is not limited thereto. That is, the dose value may be uniformized in both the channel direction and the row direction. Hereinafter, a flexible wedge filter will be described by assuming that the dose value is uniformized in both the channel direction and the row direction. In addition, in the following description, like reference numerals denote like elements as in the present embodiment, and the description thereof will be repeated only when necessary.

Figure 21:
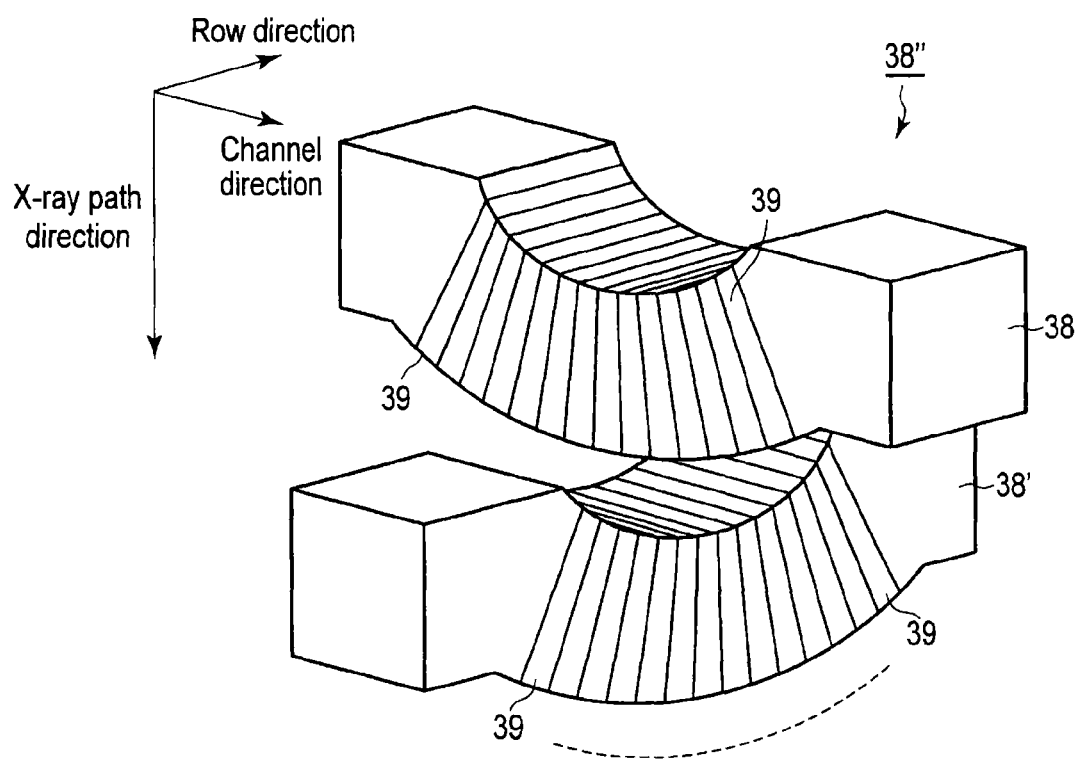
FIG. 21 is a schematic perspective view illustrating a flexible wedge filter according to Modification 4.

FIG. 21 is a schematic perspective view illustrating the flexible wedge filter 38'' according to Modification 4. As illustrated in FIG. 21, the flexible wedge filter 38'' includes a flexible wedge filter 38 having a plurality of filter modules 39 arranged in the channel direction and a flexible wedge filter 38' having a plurality of filter modules 39 arranged in the row direction. The flexible wedge filter 38 and the flexible wedge filter 38' are arranged to be perpendicular to each other. The flexible wedge filter 38 may be arranged in the X-ray tube 32 side, or the flexible wedge filter 38' may be arranged in the X-ray tube 32 side. In this manner, the flexible wedge filters 38 and 38' are supported by the module support mechanism 40 such that a pair of wedge filters 391 of each filter module 39 can approach or recede from each other in a direction perpendicular to the X-ray path direction and the arrangement direction.

In this manner, according to Modification 4, it is possible to make the dose value substantially constant in both the channel direction and the row direction. Therefore, it is possible to reduce the dynamic range in both the channel direction and the row direction.

Modification 5

In the aforementioned description, the CT gantry 3 and the PCCT gantry 5 are separate imaging mechanisms. However, the present embodiment is not limited thereto. For example, the CT gantry 3 and the PCCT gantry 5 may be integrated into a single imaging mechanism. In this case, the CT data acquisition unit 19 may be further provided in the PCCT gantry 5. In this configuration, it is possible to implement the present embodiment using a more compact configuration.

Modification 6

In the aforementioned description, the X-ray imaging apparatus is an X-ray computed tomography apparatus. However, as described above, the X-ray imaging apparatus according to the present embodiment may be an X-ray diagnosis apparatus. The X-ray diagnosis apparatus includes a C-arm instead of the rotary frames 11 and 131. The C-arm is a support mechanism that rotatably supports the X-ray tubes 12 and 32 and the X-ray detectors 13 and 33. Other parts of the configuration are similar to those of the X-ray computed tomography apparatus 1, and the description thereof will not be repeated.

Therefore, according to Modification 6, in an X-ray diagnosis apparatus having a photon counting mode, it is possible to reduce an overflow risk and a dynamic range.

Effects

As described above, in the X-ray imaging apparatus according to the present embodiment at least includes an X-ray tube 32, an X-ray detector 33, a rotation support mechanism (rotary frame) 31, a PCCT data acquisition unit 42, a flexible wedge filter 38, and a PCCT gantry controller 36. The X-ray tube 32 generates an X-ray. The X-ray detector 33 detects the X-ray that is generated from the X-ray tube 32 and transmits through an examinee P. The rotation support mechanism 31 supports the X-ray tube 32 and the X-ray detector 33. The PCCT data acquisition unit 42 acquires a set of data relating to the count of the X-ray photons for each of a plurality of energy bins included in the X-ray energy spectrum generated from the X-ray tube 32. The flexible wedge filter 38 is arranged between the X-ray tube 32 and an examinee P to attenuate the dose according to the X-ray from the X-ray tube 32. The flexible wedge filter 38 has a plurality of filter modules 39 having a configuration capable of individually changing the X-ray transmission path length in the X-ray shielding material. The PCCT gantry controller 36 individually operates the plurality of filter modules 39 such that a dose according to the X-ray incident to the X-ray detector 33 from the X-ray tube 32 via the examinee P is distributed substantially uniformly in spatial.

In this configuration, the X-ray imaging apparatus according to the present embodiment reduces a difference of the dose according to an X-ray incident to the X-ray detector 33 by substantially uniformly distributing the dose according to an X-ray incident to the X-ray detector 33 in a spatial sense. As a result, in the X-ray imaging apparatus according to the present embodiment, it is possible to reduce a dynamic range. By setting the dose according to an X-ray incident to the X-ray detector 33 to a low value such that an overflow is not easily generated, it is possible to reduce a noise included in the data of a significantly low dose and decrease an overflow risk. As a result, it is possible to implement PCCT imaging with a high reliability and a high precision.

According to the present embodiment, it is possible to reduce an overflow risk and a dynamic range.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray imaging apparatus comprising:
   an X-ray tube configured to generate an X-ray that is transmitted through an examinee;
   a photon counting detector configured to detect the X-ray generated from the X-ray tube and transmitted through the examine;
   wherein the photon counting detector detects an X-ray photon of the X-ray;
   a support mechanism configured to support the X-ray tube and the photon counting detector;
   a data acquisition unit configured to acquire a dataset relating to a count of the X-ray photon for each of a plurality of energy bands included in an energy spectrum of the X-ray generated from the X-ray tube;
   a wedge filter unit arranged between the X-ray tube and the examinee, the wedge filter unit configured to attenuate a dose according to an X-ray from the X-ray tube and include a plurality of filter modules having a configuration capable of individually changing an X-ray transmission path length in an X-ray shielding material; and
   a controller configured to individually operate the plurality of filter modules such that a dose; according to an X-ray incident to the photon counting detector from the X-ray tube via the examinee, is set based on a photon detection rate of the photon counting detector and the dose is distributed substantially uniformly in spatial.

2. The X-ray imaging apparatus according to claim 1, wherein
   the plurality of filter modules are arranged in a channel direction, and
   the controller configured to individually operate the plurality of filter modules such that a dose according to the X-ray detected by the photon counting detector is distributed substantially uniformly in the channel direction.

3. The X-ray imaging apparatus according to claim 1, wherein
   the plurality of filter modules are arranged in a direction parallel to a rotation axis of the support mechanism, and
   the controller configured to individually operate the plurality of filter modules such that a dose according to the X-ray detected by the photon counting detector is distributed substantially uniformly in a direction parallel to the rotation axis.

4. The X-ray imaging apparatus according to claim 1, wherein
   the wedge filter unit is configured to include a first filter unit and a second filter unit arranged in different positions having different distances from the X-ray tube,
   the first filter unit is configured to include a plurality of first unit filters arranged in the channel direction as the plurality of filter modules,
   the second filter unit is configured to include a plurality of second unit filters arranged in a direction parallel to the rotation axis of the support mechanism as the plurality of filter modules, and
   the controller is configured to individually operate the plurality of first unit filters and the plurality of second unit filters such that a dose according to the X-ray detected by the photon counting detector is distributed substantially uniformly in both the channel direction and a direction parallel to the rotation axis.

5. The X-ray imaging apparatus according to claim 1, further comprising:
   a computing unit configured to compute a spatial arrangement of the plurality of filter modules based on an incident dose distribution according to the X-ray, transmitting through another wedge filter having a predetermined shape and the examinee, detected by the photon counting detector, wherein
   the controller is configured to individually move the plurality of filter modules based on a spatial arrangement of the plurality of filter modules.

6. The X-ray imaging apparatus according to claim 1, further comprising:
   a computing unit configured to compute a spatial arrangement of the plurality of filter modules based on an incident dose distribution according to the X-ray, transmitting through another wedge filter having a predetermined shape and the examinee, detected by the photon counting detector and an incident dose distribution according to the X-ray, transmitting through only the examinee, detected by the photon counting detector, wherein
   the controller individually moves the plurality of filter modules based on the spatial arrangement of the plurality of filter modules.

7. The X-ray imaging apparatus according to claim 1, wherein the controller is configured to individually operate the plurality of filter modules for each view.

8. The X-ray imaging apparatus according to claim 1, further comprising:
   a movement support mechanism configured to individually movably support each of the plurality of filter modules.

9. The X-ray imaging apparatus according to claim 8, wherein
   each of the plurality of filter modules configured to include a pair of wedge-like filters having a wedge shape,
   the movement support mechanism configured to support the pair of wedge-like filters such that slope surfaces of the wedge face each other, and
   the controller is configured to drive the movement support mechanism such that the pair of wedge-like filters approach or recede from each other, in order to change an X-ray transmission path length transmitting through the pair of wedge-like filters.

10. The X-ray imaging apparatus according to claim 9, wherein the movement support mechanism configured to support the pair of wedge-like filters such that the pair of wedge-like filters approach or recede from each other in a direction perpendicular to a path of the X-ray irradiated from the X-ray tube and an arrangement direction of the plurality of filter modules.

11. A method of controlling a wedge filter apparatus including a plurality of filter modules configured to be arranged between an X-ray tube and an examinee to attenuate a dose according to an X-ray from the X-ray tube and include a plurality of filter modules having a configuration capable of individually changing an X-ray transmission path length in an X-ray shielding material, the method comprising:
   computing a movement amount of each of the plurality of filter modules such that a dose according to an X-ray incident to a photon counting detector from the X-ray tube via the examinee, is set based on a photon detection rate of the photon counting detector and the dose is distributed substantially uniformly in spatial and
   individually operating the plurality of filter modules based on the computed movement amount.

12. An X-ray imaging apparatus, comprising:
   an X-ray tube configured to generate an X-ray that is transmitted through an examinee;
   an X-ray detector configured to detect the X-ray generated from the X-ray tube and transmitted through the examinee;
   a support mechanism configured to support the X-ray tube and the X-ray detector;
   a data acquisition unit configured to acquire a dataset relating to a count of an X-ray photon for each of a plurality of energy bands included in an energy spectrum of the X-ray generated from the X-ray tube;
   a wedge filter unit arranged between the X-ray tube and the examinee, the wedge filter unit configured to attenuate a dose according to an X-ray from the X-ray tube and the wedge filter unit including a plurality of filter modules having a configuration capable of individually changing an X-ray transmission path length in an X-ray shielding material;
   a movement support mechanism configured to individually movably support each of the plurality of filter modules; and
   a controller configured to individually operate the plurality of filter modules such that a dose, according to an X-ray incident to the X-ray detector from the X-ray tube via the examinee is distributed substantially uniformly in spatial, wherein
   each of the plurality of filter modules is configured to include a pair of wedge-like filters having a wedge shape, a predetermined filter module among the plurality of filter modules further including a fixed filter,
   the movement support mechanism is configured to support the pair of wedge-like filters such that slope surfaces of the wedge face each other, and support the fixed filter such that an X-ray transmission path through the pair of wedge-like filters intersects with the fixed filter, and
   the controller is configured to drive the movement support mechanism such that the pair of wedge-like filters approach or recede from each other, in order to change an X-ray transmission path length transmitting through the pair of wedge-like filters.

* * * * *